(12) United States Patent
Sorgenfrei et al.

(10) Patent No.: US 9,625,404 B2
(45) Date of Patent: Apr. 18, 2017

(54) SYSTEMS AND METHODS FOR SINGLE-MOLECULE DETECTION USING NANOTUBES

(71) Applicant: The Trustees of Columbia University in the City of New York, New York, NY (US)

(72) Inventors: Sebastian Sorgenfrei, Portland, OR (US); Kenneth Shepard, Ossining, NY (US); Chien-Yang Chiu, Goleta, CA (US); Colin Nuckolls, New York, NY (US); Steven Warren, White Plains, NY (US)

(73) Assignee: The Trustees Of Columbia University In the City of New York, New York, NY (US)

( * ) Notice: Subject to any disclaimer, the term of this patent is extended or adjusted under 35 U.S.C. 154(b) by 751 days.

(21) Appl. No.: 13/801,834

(22) Filed: Mar. 13, 2013

(65) Prior Publication Data
US 2013/0285680 A1  Oct. 31, 2013

Related U.S. Application Data

(63) Continuation-in-part of application No. PCT/US2012/020955, filed on Jan. 11, 2012.
(Continued)

(51) Int. Cl.
*G01N 27/327* (2006.01)
*G01N 27/04* (2006.01)
*C12Q 1/68* (2006.01)

(52) U.S. Cl.
CPC ......... *G01N 27/041* (2013.01); *C12Q 1/6816* (2013.01); *C12Q 1/6874* (2013.01); *G01N 27/3278* (2013.01)

(58) Field of Classification Search
CPC .............. G01N 27/04; G01N 27/227; G01N 27/3275–27/3277; B82Y 15/00; C01B 31/022
See application file for complete search history.

(56) References Cited

U.S. PATENT DOCUMENTS 5,304,950 A  4/1994  Martin et al.
5,599,668 A  2/1997  Stimpson et al.
(Continued)

FOREIGN PATENT DOCUMENTS

CN  101126735 A  2/2008
CN  101194162 A  6/2008
(Continued)

OTHER PUBLICATIONS

X. Guo, et al. "Functional single-molecule devices based on SWNTs as point contacts" Journal of Materials Chemistry, vol. 19, 2009, p. 5470-5473.*
(Continued)

*Primary Examiner* — J. Christopher Ball
(74) *Attorney, Agent, or Firm* — Baker Botts L.L.P.

(57) ABSTRACT

A method for single-molecule detection is provided and uses a carbon nanotube having a probe entity attached thereto to define a first state of the carbon nanotube. The carbon nanotube is introduced to a target entity to define a second state of the carbon nanotube. The electrical conductance of the carbon nanotube in the first and second states is compared to detect the presence of a biomolecular entity. A system for single-molecule detection including a carbon nanotube is also provided.

19 Claims, 25 Drawing Sheets

Related U.S. Application Data

(60) Provisional application No. 61/431,795, filed on Jan. 11, 2011, provisional application No. 61/453,344, filed on Mar. 16, 2011.

(56) References Cited

U.S. PATENT DOCUMENTS

| | | | |
|---|---|---|---|
| 6,030,115 | A | 2/2000 | Ishiguro et al. |
| 7,056,670 | B2 | 6/2006 | Odedra |
| 7,208,077 | B1 | 4/2007 | Albers et al. |
| 7,468,271 | B2 | 12/2008 | Golovchenko et al. |
| 7,491,628 | B2 | 2/2009 | Noca et al. |
| 7,635,423 | B2 | 12/2009 | Boussad et al. |
| 7,666,593 | B2 | 2/2010 | Lapidus |
| 7,767,400 | B2 | 8/2010 | Harris |
| 7,790,391 | B2 | 9/2010 | Harris et al. |
| 7,948,015 | B2 | 5/2011 | Rothberg et al. |
| 8,013,366 | B2 | 9/2011 | Lee et al. |
| 8,038,943 | B2 | 10/2011 | Yoo et al. |
| 9,194,801 | B2 | 11/2015 | Shepard et al. |
| 2002/0006357 | A1 | 1/2002 | McGeoch et al. |
| 2002/0022226 | A1 | 2/2002 | Nakao et al. |
| 2003/0087292 | A1 | 5/2003 | Chen et al. |
| 2004/0028875 | A1 | 2/2004 | Van Rijn et al. |
| 2004/0055901 | A1 | 3/2004 | Petersen et al. |
| 2004/0238379 | A1 | 12/2004 | Lindsay et al. |
| 2005/0145496 | A1 | 7/2005 | Goodsaid et al. |
| 2005/0181383 | A1 | 8/2005 | Su et al. |
| 2005/0191495 | A1 | 9/2005 | Rueckes et al. |
| 2006/0078468 | A1 | 4/2006 | Gabriel et al. |
| 2006/0194263 | A1 | 8/2006 | Boussad et al. |
| 2006/0240543 | A1 | 10/2006 | Folch et al. |
| 2006/0246443 | A1 | 11/2006 | Bockelmann et al. |
| 2006/0246497 | A1 | 11/2006 | Huang et al. |
| 2007/0292855 | A1 | 12/2007 | Dubin et al. |
| 2008/0035494 | A1 | 2/2008 | Gomez et al. |
| 2008/0094076 | A1 | 4/2008 | Hibbs et al. |
| 2008/0191718 | A1 | 8/2008 | Wolkow et al. |
| 2008/0203380 | A1 | 8/2008 | Wang et al. |
| 2008/0214494 | A1 | 9/2008 | Mohapatra et al. |
| 2008/0274912 | A1 | 11/2008 | Johnson et al. |
| 2009/0026082 | A1 | 1/2009 | Rothberg et al. |
| 2009/0142504 | A1 | 6/2009 | Ervin et al. |
| 2009/0173527 | A1 | 7/2009 | Benke et al. |
| 2009/0181381 | A1 | 7/2009 | Oldham et al. |
| 2009/0305319 | A1 | 12/2009 | Baudenbacher et al. |
| 2009/0325350 | A1 | 12/2009 | Radosavljevic et al. |
| 2010/0088040 | A1 | 4/2010 | Johnson, Jr. |
| 2010/0148126 | A1 | 6/2010 | Guan et al. |
| 2010/0285637 | A1 | 11/2010 | Khan et al. |
| 2010/0327874 | A1 | 12/2010 | Liu et al. |
| 2010/0331194 | A1 | 12/2010 | Turner et al. |
| 2011/0057725 | A1 | 3/2011 | Ikeda et al. |
| 2011/0101996 | A1 | 5/2011 | Potyrailo et al. |
| 2011/0105870 | A1 | 5/2011 | Dale et al. |
| 2011/0147714 | A1 | 6/2011 | Hong et al. |
| 2011/0220775 | A1 | 9/2011 | Triener et al. |
| 2011/0263463 | A1 | 10/2011 | Rothberg et al. |
| 2012/0025414 | A1 | 2/2012 | Schmidt et al. |
| 2012/0061239 | A1 | 3/2012 | Elibol et al. |
| 2012/0064519 | A1 | 3/2012 | Fang et al. |
| 2012/0234679 | A1 | 9/2012 | Garaj et al. |
| 2013/0180867 | A1 | 7/2013 | Rosenstein et al. |
| 2013/0285680 | A1 | 10/2013 | Sorgenfrei et al. |
| 2014/0048416 | A1 | 2/2014 | Rosenstein et al. |
| 2015/0090588 | A1 | 4/2015 | Shepard et al. |
| 2015/0093849 | A1 | 4/2015 | Shepard et al. |
| 2015/0369776 | A1 | 12/2015 | Rosenstein et al. |

FOREIGN PATENT DOCUMENTS

| | | | |
|---|---|---|---|
| CN | 101346472 A | | 1/2009 |
| WO | WO 2006/024023 A2 | | 3/2006 |
| WO | WO 2007/075967 A2 | | 7/2007 |
| WO | WO 2008/132643 | | 11/2008 |
| WO | WO 2009/046110 A1 | | 4/2009 |
| WO | WO 2010/030057 A1 | | 3/2010 |
| WO | WO 2011/123525 | | 10/2011 |
| WO | WO 2012/021149 A1 | | 2/2012 |
| WO | WO 2012/042226 A2 | | 4/2012 |
| WO | WO 2012/044857 A2 | | 4/2012 |

OTHER PUBLICATIONS

A.K. Feldman, et al. "Molecular Electronic Devices Based on Single-Walled Carbon Nanotube Electrodes" Accounts of Chemical Research, vol. 41, No. 12, Dec. 2008, p. 1731-1741.*
U.S. Appl. No. 13/942,242, filed Jul. 15, 2013.
International Search Report and Written Opinion for PCT/US2013/031757, dated Jun. 4, 2013.
International Search Report and Written Opinion for PCT/US2013/031745, dated Jun. 4, 2013.
International Search Report and Written Opinion for PCT/US2012/026292, dated May 29, 2012.
International Search Report and Written opinion for PCT/US2012/020955, dated May 16, 2012.
Suzuki, et al., "Microtechnologies for membrane protein studies", *Anal Bioanal Chem.*, 391(8):2695-2702 (2008).
U.S. Appl. No. 13/787,341, filed Jan. 15, 2015.
CN Office Action dated Nov. 19, 2014 in CN Patent Application No. 201280004265.8.
Extended EP Search Report dated Dec. 15, 2014 in EP Application No. 12734088.
Besteman, K. et al., "Enzyme-coated carbon nanotubes as single molecule biosensors", Nano Letters, *American Chemical Society*, vol. 3, No. 6, Jan. 5, 2003, pp. 727-730, XP002982648.
Dongliang, Fu et al., "Label-free electrical detection of DNA hybridization using carbon nanotubes and graphene", *NANO Reviews*, vol. 1, No. 0, Aug. 31, 2010, XP055158479.
Hye-Mi, So et al., "Single-Walled Carbon Nanotube Biosensors Using Aptamers as Molecular Recognition Elements", *Journal of the American Chemical Society*, vol. 127, No. 34, Aug. 1, 2005, pp. 11906-11907, XP55032046.
Miron, Hazani et al., "Confocal Fluorescence Imaging of DNA-Functionalized Carbon Nanotubes", *Nano Letters*, vol. 3, No. 2, Feb. 1, 2003, pp. 153-155, XP055157827.
Sebastian, Sorgenfrei et al., "Label-free single-molecule detection of DNA-hybridization kinetics with a carbon nanotube field-effect transistor", *Nature Nanotechnology*, vol. 6, No. 2, Jan. 23, 2011, pp. 126-132, XP055157740.
Star, A. et al., "Label-free detection of DNA hybridization using carbon nanotube network field-effect transistors", *Proceedings of the National Academy of Sciences*, vol. 103, No. 4, Jan. 24, 2006, pp. 921-926, XP003023787.
Yin et al. (IEEE, 2007).
U.S. Appl. No. 13/787,341, Jun. 12, 2015 Notice of Allowance.
U.S. Appl. No. 13/787,341, Apr. 14, 2015 Response to Non-Final Office Action.
U.S. Appl. No. 13/942,242, Jul. 30, 2015 Notice of Abandonment.
U.S. Appl. No. 13/942,242, Jan. 22, 2015 Non-Final Rejection.
CN Office Action dated Jul. 10, 2015 in CN Patent Application No. 201280004265.8.
U.S. Appl. No. 13/787,341, Nov. 16, 2015 Issue Fee Payment.
U.S. Appl. No. 13/787,341, Aug. 20, 2015 Notice of Allowance.
U.S. Appl. No. 13/787,341, Aug. 12, 2015 Request for Continued Examination (RCE).
U.S. Appl. No. 13/787,341, Jan. 15, 2015 Non-Final Office Action.
U.S. Appl. No. 13/595,106, Sep. 24, 2015 Issue Fee Payment.
U.S. Appl. No. 13/595,106, Jun. 24, 2015 Notice of Allowance.
U.S. Appl. No. 13/595,106, Dec. 18, 2014 Request for Continued Examination (RCE).
U.S. Appl. No. 13/595,106, Dec. 18, 2014 Response after Final Office Action.
U.S. Appl. No. 13/595,106, Oct. 6, 2014 Applicant Initiated Interview Summary.
U.S. Appl. No. 13/595,106, Jun. 25, 2014 Final Office Action.

(56) References Cited

OTHER PUBLICATIONS

U.S. Appl. No. 13/595,106, May 5, 2014 Response to Non-Final Office Action.
U.S. Appl. No. 13/595,106, Apr. 25, 2014 Applicant Initiated Interview Summary.
U.S. Appl. No. 13/595,106, Feb. 5, 2014 Non-Final Office Action.
U.S. Appl. No. 13/595,106, Dec. 9, 2013 Response to Restriction Requirement.
U.S. Appl. No. 13/595,106, Jul. 25, 2013 Restriction Requirement Filed.
U.S. Appl. No. 14/509,766, Apr. 20, 2016 Non-Final Office Action.
Anderson, et al., "A Label-free CMOS DNA Microarray based on Charge Sensing," Instrumentation and Measurement Technology Conference Proceedings, May 12-15, 2008, pp. 1631-1636.
Arata, et al., "Millisecond Analysis of Double Stranded DNA with Flourescent Intercalator by Micro-Thermocontrol-Device'," Talanta, 79(3):963-966 (2009).
Barilero et al "Fluorescent thermometers for dual-emission wavelength measurements: Molecular engineering and application to thermal imaging in a microsystem," Analytical Chemistry, 81(19): 7988-8000 (2009).
Barilero et al Analytical Chemistry, 2009, 81: supplemental information.
Goldsmith, et al., "Conductance-Controlled Point Functionalization of Single-Walled Carbon Nanotubes," Science 315(5808):77-81 (2007).
Goldsmith, et al., "Monitoring Single-Molecule Reactivity on a Carbon Nanotube," Nano Letters 8(1):189-194 (2008).
Gudnason, et al., "Comparison of Multiple DNA Dyes for Real-Time PCR: Effects of Dye Concentration and Sequence Composition on DNA Amplification and Melting Temperature," Nucleic Acids Research, 35(19):e127 (2007).
Heller, et al., "Identifying the mechanism of biosensing with carbon nanotube transistors," Nano Letters 8(2):591-5 (2008).
Huang, et al., "Gene expression analysis with an integrated CMOS microarray by time-resolved fluorescence detection," Biosensors and Bioelectronics 26:2660-2665 (2011).
Kang, et al., "High-performance electronics using dense, perfectly aligned arrays of single-walled carbon nanotubes," Nat Nano 2(4):230-236 (2007).
Kim, et al., "Nanopore sensor for fast label-free detection of short double-stranded DNAs," Biosensors and Bioelectronics 22(12):2926-2931 (2007).
Levine, et al., "Real-time, multiplexed electrochemical DNA detection using an active complementary metal-oxide-semiconductor biosensor array with integrated sensor electronics," Biosensors and Bioelectronics 24(7):1995-2001 (2009).
Liu et al., "Translocation of Single-Stranded DNA Through Single-Walled Carbon Nanotubes," Science 327(5961):64-67 (2010).
Meric, et al., "Hybrid carbon nanotube-silicon complementary metal oxide semiconductor circuits," Journal of Vacuum Science & Technology B 25(6):2577-2580 (2007).
Mortazavi, et al., "Mapping and quantifying mammalian transcriptomes by RNA-Seq.," Nature Methods 5(7): 621-628 (2008).
Polk, et al., "Ag/AgCl microelectrodes with improved stability for microfluidics," Sensors & Actuators: B. Chemical 114:239-247 (2006).
Rosenblatt, et al., "High performance electrolyte gated carbon nanotube transistors," Nano Letters 2(8):869-872 (2002).
Rosenstein, et al., "Integrated nanopore sensing platform with sub-microsecond temporal resolution," Nature Methods 9(5):487-494 (May 2012).
Sorgenfrei, et al., "Debye Screening in Single-Molecule Carbon Nanotube Field-Effect Sensors," Nano Letters 11(9):3739-3743 (2011).
Sorgenfrei, et al., "Single-molecule electronic detection using nanoscale field-effect devices," Design Automation Conference (DAC), Jun. 5-9, 2011.
Tashiro, et al., "A Nanothermometer Based on the Different pi Stacking of B- and Z-DNA," Angewandte Chemie International Edition, 42(18):6018-6020 (2003).
Tashiro, et al., "The Molecular-Thermometer Based on B-Z-Transition of DNA," Nucleic Acids Symposium Series, 48(1):89-90 (2004).
Wanunu, et al., "Electrostatic focusing of unlabelled DNA into nanoscale pores using a salt gradient," Nat Nano 5(2):160-165 (2010).
Yin et al., "A Low-Noise Preamplifier with Adjustable Gain and Bandwidth for Biopotential Recording Applications", IEEE, 2007, pp. 321-324.
Zhao, et al., "Stochastic sensing of biomolecules in a nanopore sensor array," Nanotechnology 19(50):505504 (8pp) (2008).

\* cited by examiner

SYSTEMS AND METHODS FOR SINGLE-MOLECULE DETECTION USING NANOTUBES

CROSS-REFERENCE TO RELATED APPLICATIONS

This application is a continuation-in-part of International Application No. PCT/US2012/020955, filed Jan. 11, 2012, which claims priority to U.S. Provisional Patent Application No. 61/431,795, filed Jan. 11, 2011 and U.S. Provisional Patent Application No. 61/453,344, filed Mar. 16, 2011, each of which is incorporated by reference herein in its entirety.

This invention was made with government support under grant numbers ENG-0707748 and CHE-0641523, awarded by the National Science Foundation, grant number N000 14-09-1-0250 awarded by the Office of Naval Research and grant number HG006882 awarded by the National Istitute of Health (NIH). The government has certain rights in the invention.

BACKGROUND

The present application relates to the detection of single-molecules and the measurement and analysis of single-molecule kinetics and thermodynamics.

Studies at the single molecule level have revealed intramolecular dynamics and conformational changes in many biomolecular systems. The intramolecular chain diffusion of nucleic acids, including the hairpin configuration, has been studied by optical techniques such as fluorescence correlation spectroscopy (FCS). In certain studies, labels are attached to the DNA hairpin and the opening and closing rates of a small number of molecules can be monitored at sub-microsecond time-scales. One of the potential disadvantages of FCS, however, can be that observation time is limited to the diffusion time of molecules through the observation volume. Single-molecule fluorescence resonance energy transfer (smFRET) has also been used to study conformational changes in biomolecules but provides only tens of millisecond time-scales for kinetic studies. Label-free technologies for biomolecular detection include nanowires, microcavities, mechanical cantilevers, optical waveguides and optical tweezers, but none have combined high enough sensitivity for label-free detection with the high temporal resolution necessary to monitor the kinetics of biomolecular processes to microsecond time-scales.

Certain single-molecule-based sequencing-by-synthesis (SBS) systems have become commercially used because they can function without amplification, simplifying sample preparation. Because of their use of fluorescence, certain system designs involves complex trade-offs in the design of the dyes and dye chemistries, laser excitation systems, optics and filtering, and detector characteristics. These challenges can stem from the use of photons as an intermediary for detection, when ultimately an electrical signal is required by the detection electronics.

SUMMARY

Disclosed herein are new and improved systems and methods for single-molecule detection.

In one embodiment, the disclosed subject matter provides single-molecule detection based on the conductance modulation of a carbon nanotube. The conductance of the carbon nanotube can be compared based on an initial state of the carbon nanotube and a second state of the carbon nanotube after introduction to a target entity.

In one embodiment of the disclosed subject matter, a method for single-molecule detection uses a carbon nanotube having a probe entity attached thereto to define a first state of the carbon nanotube. The carbon nanotube can be introduced to a target entity to define a second state of the carbon nanotube. The electrical conductance of the carbon nanotube in the first and second states can be compared to detect the presence of a biomolecular entity.

In some embodiments, the probe entity is attached to the carbon nanotube by applying a point defect to the carbon nanotube and attaching the probe entity to the carbon nanotube at the point defect. The one point defect can be a single carboxyl defect. The probe entity can be attached to the carbon nanotube via a coupling reaction. The probe entity can be a probe DNA, which can comprise ssDNA. The target entity can be a complementary target DNA.

In some embodiments, the probe entity can include a protein. The target entity can include a target protein to bind to the probe protein. The probe entity can include an enzyme. The enzyme can include DNA polymerase or RNA polymerase. The target entity can include newly incorporated nucleotides in a synthesized sequence. One or more conformational changes of the DNA polymerase or RNA polymerase can define the second state relative to the first state.

In some embodiments, the carbon nanotube can be introduced to the target entity in a buffer composition containing the target entity.

In some embodiments, the electrical conductance of the carbon nanotube in the first and second states can be compared to predetermined conductance data to ascertain the identity of the target entity. The predetermined conductance data can be a calibration curve.

In some embodiments, the carbon nanotube can be a single-walled carbon nanotube. The carbon nanotube can be a field effect transistor that provides an electronic signal for measuring the conductance in the first and second states of the carbon nanotube.

In some embodiments, the method for single-molecule detection is label free.

In some embodiments, the method for single-molecule detection is used to provide single-molecule, sequencing-by-synthesis (SBS) of a biomolecule. The biomolecule can be DNA.

In another embodiment, a system for single-molecule detection includes a carbon nanotube having a probe entity attached thereto, a field effect transistor in electronic communication with the carbon nanotube, and a supply of a target entity.

The accompanying drawings, which are incorporated and constitute part of this disclosure, illustrate embodiments of the disclosed subject mater and serve to explain its principles.

BRIEF DESCRIPTION OF THE DRAWINGS

Further features, the nature, and various advantages of the disclosed subject matter will be more apparent from the following detailed description of the embodiments and the accompanying drawings in which:

FIG. 4b is a series of conductance based-histograms for the recordings of FIG. 4a;

FIGS. 4c-1 and 4c-2 are a series of graphs of conductance recordings after introduction to a target entity in accordance with some embodiments of the disclosed subject matter;

Figure 1:
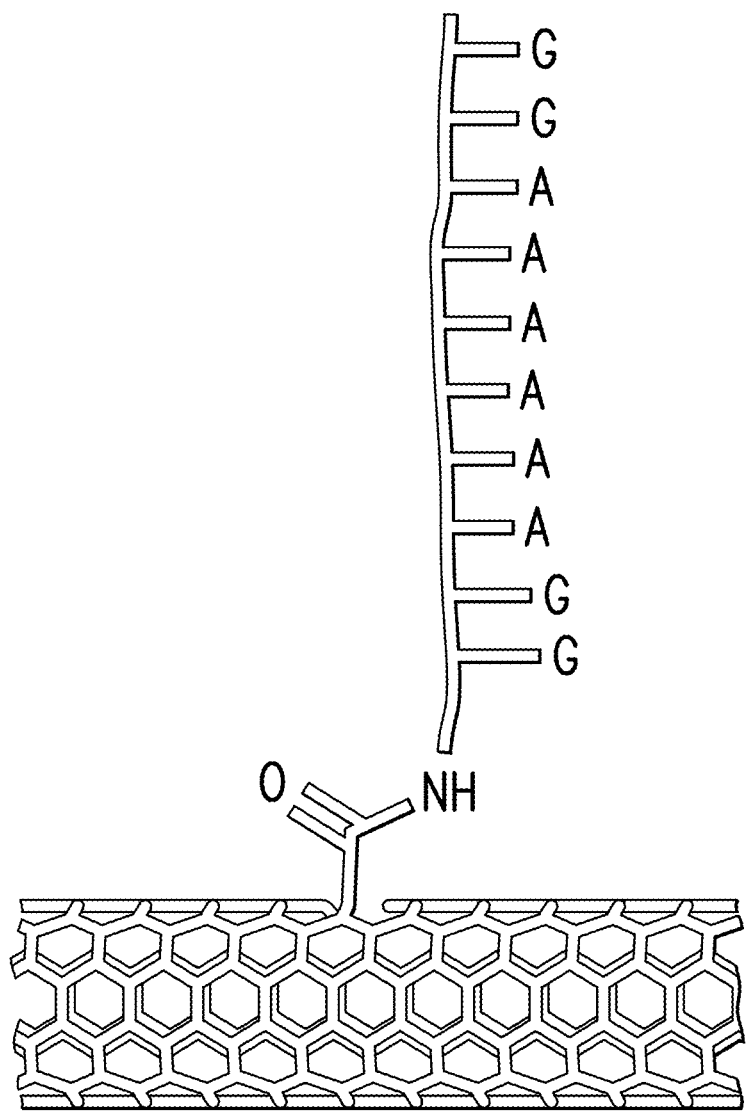
FIG. 1 is a diagram of an exemplary carbon nanotube in accordance with some embodiments of the disclosed subject matter.

Throughout the drawings, the same reference numerals and characters, unless otherwise stated, are used to denote like features, elements, components or portions of the illustrated embodiments. Moreover, while the present disclosed subject matter will now be described in detail with reference to the Figures, it is done so in connection with the illustrative embodiments.

DETAILED DESCRIPTION

New and improved techniques are provided for single-molecule detection utilizing carbon nanotubes. In some embodiments, the new systems and methods are label free and avoid the drawbacks of using labels as described above and provide for improved bandwidth One-dimensional (1D) conductors such as single-walled carbon nanotubes (SWCNTs or CNTs) can act as high-gain field-effect sensors whose conductance varies strongly with local charge density. In accordance with one aspect of the disclosed subject matter, single point defects can be electrochemically created in such carbon nanotubes in a controllable manner and can be used to covalently bind biomolecules at the scattering site, as is described below in more detail. Such resulting carbon nanotubes transistors (or "devices") exhibit sensitivity to the binding of a single molecule (e.g., with a conductance change of more than 100 nS for binding of a reactive carbodiimide), due to Coulomb interaction between the molecule and the defect which modulates scattering in the 1D channel. Thus these devices can be prepared with high yields due to the real-time monitoring of conductance during defect generation, as described below. The defect-dominated conductance in the nanotubes can be used to detect the presence of a biomolecular entity and sufficiently high signal-to-noise ratio (SNR) and bandwidth can be achieved to measure single-molecule DNA hybridization kinetics and thermodynamics. As such, the detection can be through a label-free field-effect-based approach.

For the purpose of illustration and not limitation, FIG. 1 is a diagram of a carbon nanotube in accordance with the disclosed subject matter. The carbon nanotube 101 has a probe entity 102, such as DNA, attached thereto. The probe entity can be attached to the carbon nanotube by applying a point defect 103, such as a carboxyl defect, to the carbon nanotube. The carbon nanotube 101 shown in FIG. 1 defines a first state of the carbon nanotube.

Figure 2:
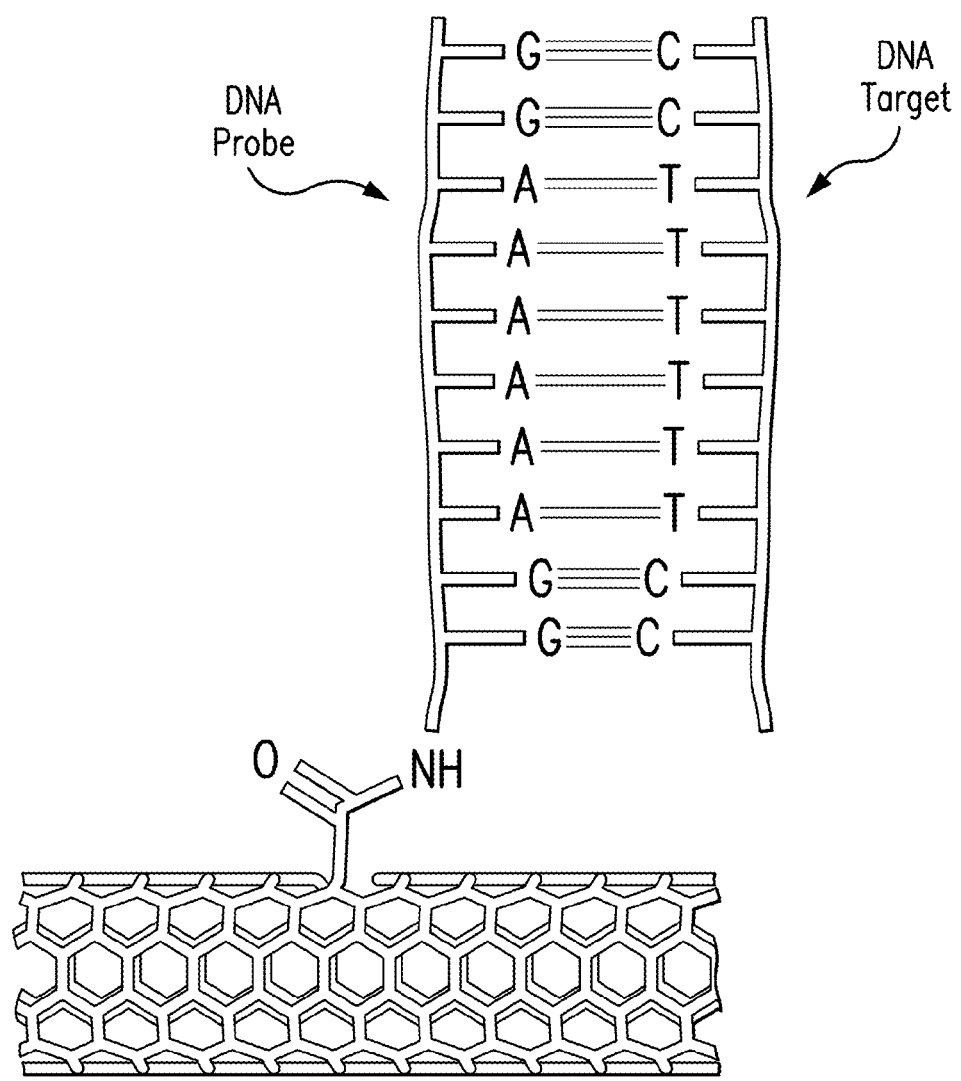
FIG. 2 is a diagram of carbon nanotube after introduction of a target entity in accordance with some embodiments of the disclosed subject matter.

The carbon nanotube 101 is introduced to a target entity to define a second state of the carbon nanotube. For the purpose of illustration and not limitation, FIG. 2 is a diagram of a carbon nanotube 101 having a probe DNA 102 attached thereto at a point defect 103 after introduction to a target entity 104. In accordance with the disclosed subject matter, the electrical conductance of the carbon nanotube in the first and second states is compared to detect the presence of a biomolecular entity, as described below in more detail.

The carbon nanotube transistors in accordance with the disclosed subject matter can be fabricated using standard fabrication techniques. For example and without limitation, carbon nanotubes with a diameter less than 2 nm can be grown by chemical vapor deposition on degenerately doped silicon wafers with 300 nm of thermally grown silicon oxide and contacted by multiple titanium electrodes using optical lithography. Oxygen plasma ion etching can be used on a selectively exposed area in a second lithography procedure to electrically isolate neighboring devices, leaving only one nanotube between a pair of electrodes. After fabrication, the devices can be placed in an electrochemical cell, contacted by fixed wire-bonds that are encapsulated with epoxy and sealed with a small glass tube. A platinum counter electrode can be used in a pseudo-reference configuration to control the liquid potential both during oxidation and in subsequent aqueous experiments.

The point functionalization of the nanotubes can be achieved using any electrochemical method known to one of skill in the art. For example and without limitation, an oxidation potential, slightly greater than the oxidation threshold (between −0.9 and −1V), can be applied through the platinum electrode in sulfuric acid (e.g., 1M $H_2SO_4$ in deionized water) until a sharp drop in the nanotube conductance is observed. For example, the oxidation can be terminated at about a 90% or 99% reduction in the conduction level. When oxidation is terminated at a 90% reduction in the conduction level, about 88% of the devices remain conductive out of which about 19% yield functional single molecule devices. At a greater than 99% reduction in the conductance level, the percentage of conductive devices decreases to about 18% out of which about 28% yield functional single molecule devices. Without being bound by theory, the lower yield in this final procedure can be attributed to a number of factors including the possibility of generating unreactive CO and C=O defects, multiple reactive defects and over-oxidation that yields insulating devices.

Figure 3A:
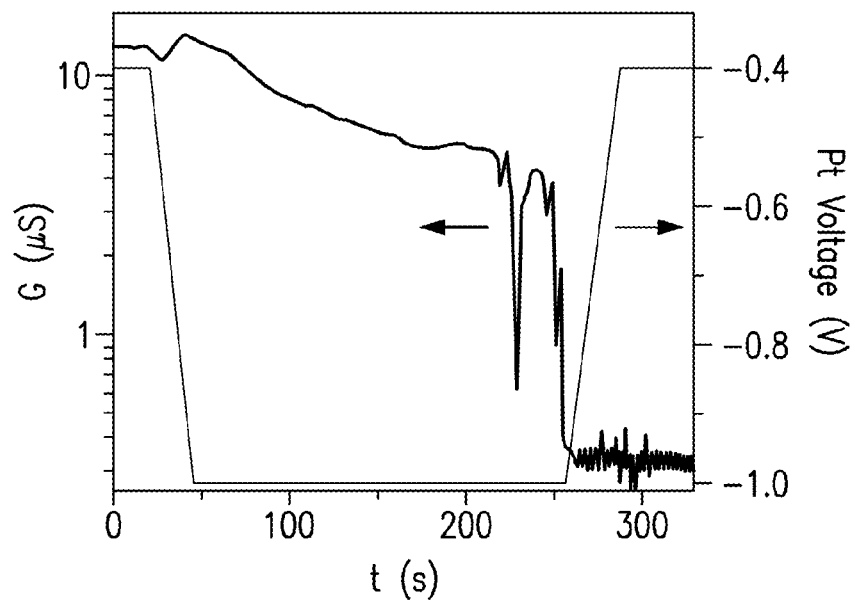
FIG. 3a is a graph showing conductance-controlled oxidation of a nanotube in accordance with some embodiments of the disclosed subject matter.

For the purpose of illustration and not limitation, FIG. 3a shows a typical conductance-controlled oxidation in 1 M $H_2SO_4$ (aqueous) with 30 mV bias. After the drop in device conductance, the oxidation potential can be reduced and the device can be immersed in 6.5 mM $KMnO_4$ in order to create a carboxyl functional group on the freshly created defect. The resulting single molecule functional devices are characterized by the two-level conductance fluctuations described below when functionalized with probe DNA in the presence of complementary target.

Figure 3B:
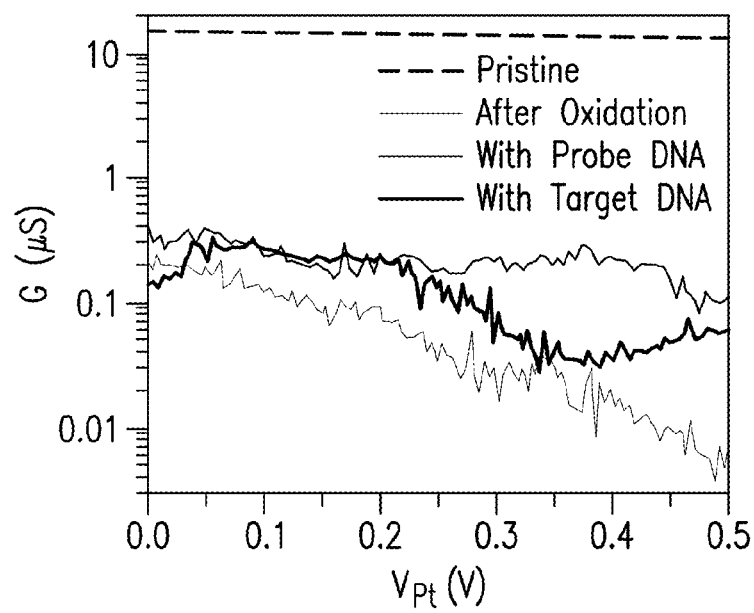
FIG. 3b is a graph showing conductance as function of potential in accordance with some embodiments of the disclosed subject matter.
Figure 3C:
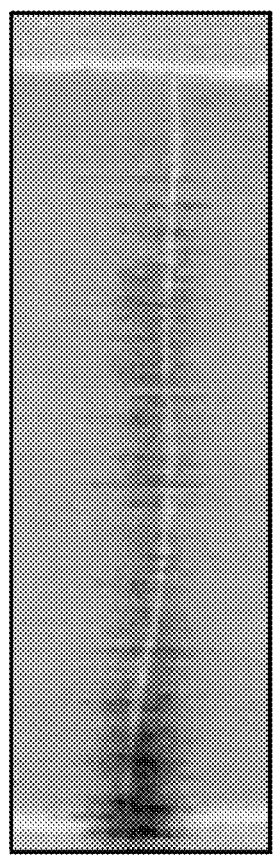
FIGS. 3c and 3d are topography scanning gate microscopy (SGM) images of a semiconducting nanotube in accordance with some embodiments of the disclosed subject matter.
Figure 3D:
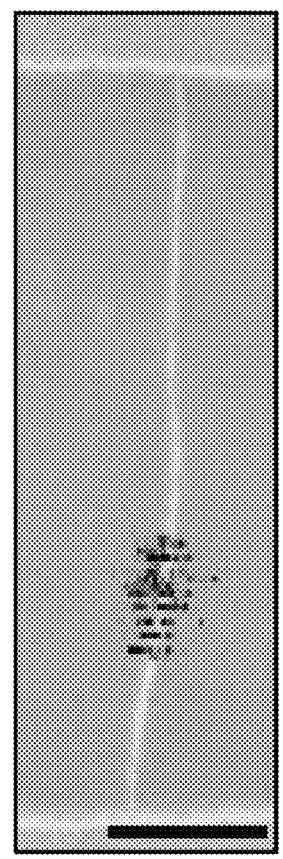

The local defects generated by this process can be investigated using scanning gate microscopy (SGM) of the nanotube before and after oxidation. By applying a local gate through the cantilever of an atomic force microscopy (AFM) to a small region of the nanotube while monitoring the conductance, the sensitivity of the conductance to local gating can be spatially mapped out. For the purpose of illustration and not limitation, FIGS. 3c and 3d show SGM images overlaid with the device topography before and after oxidation, respectively. The scale bar is 500 nm. In the overlayed SGM image, the darker area corresponds to lower current at a fixed bias voltage of 100 mV. This device is a semiconducting nanotube, and FIG. 3c shows that the Schottky barriers at the contacts dominate the device's gate sensitivity. After oxidation, however, the sensitivity is localized to the location of the defect on the nanotube and no longer depends on the initial band structure as shown in FIG. 3d. Both metallic and semiconducting nanotube devices can be used and generally show large gate dependence after oxidation. For the purpose of illustration, FIG. 3b shows a representative current-voltage (I-V) characteristic of a device in its pristine state and after oxidation. FIG. 3b shows the conductance as a function of potential on the PT electrode relative to the source-drain potential of the nanotube ($V_{pt}$) at different stages in the process: before oxidation, after oxidation, after overnight coupling with probe DNA and after exposure to target DNA at 100 mV source-drain bias. Initially the nanotube is metallic but it shows a large gate response after oxidation.

Figure 3E:
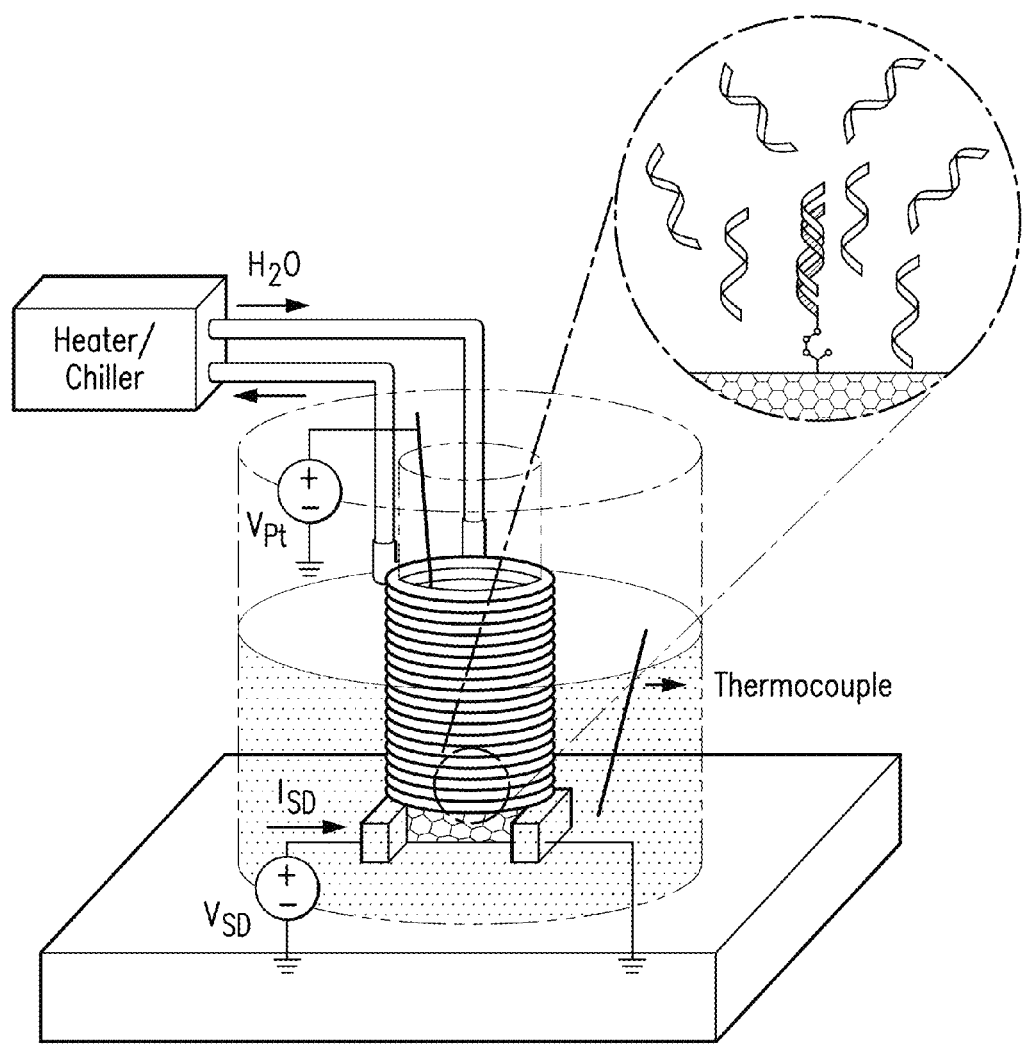
FIG. 3e is a schematic of a nanotube device in accordance with some embodiments of the disclosed subject matter.
Figure 4A:
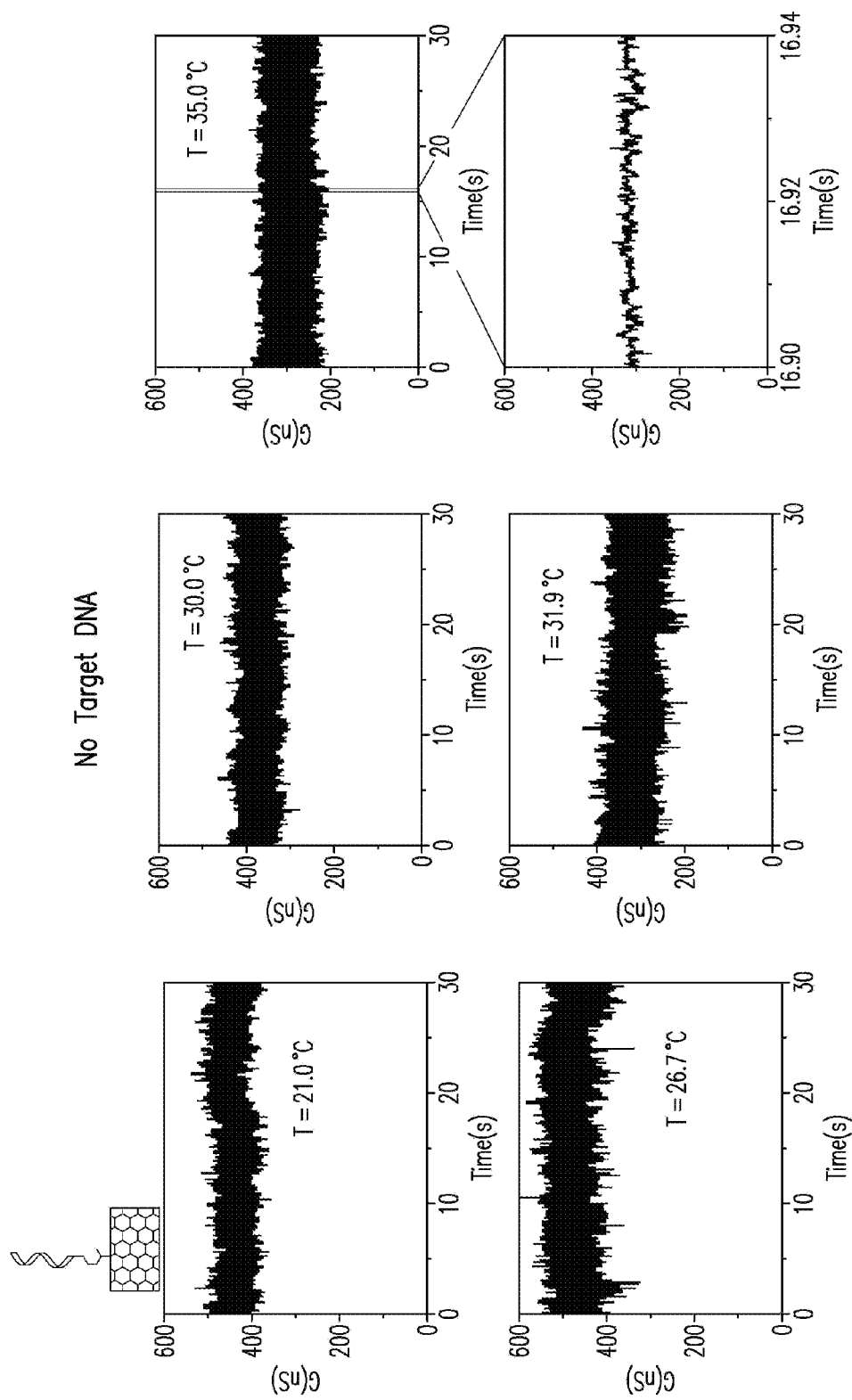
FIG. 4a is a series of graphs of conductance recordings before introduction to a target entity in accordance with some embodiments of the disclosed subject matter.
Figure 4B:
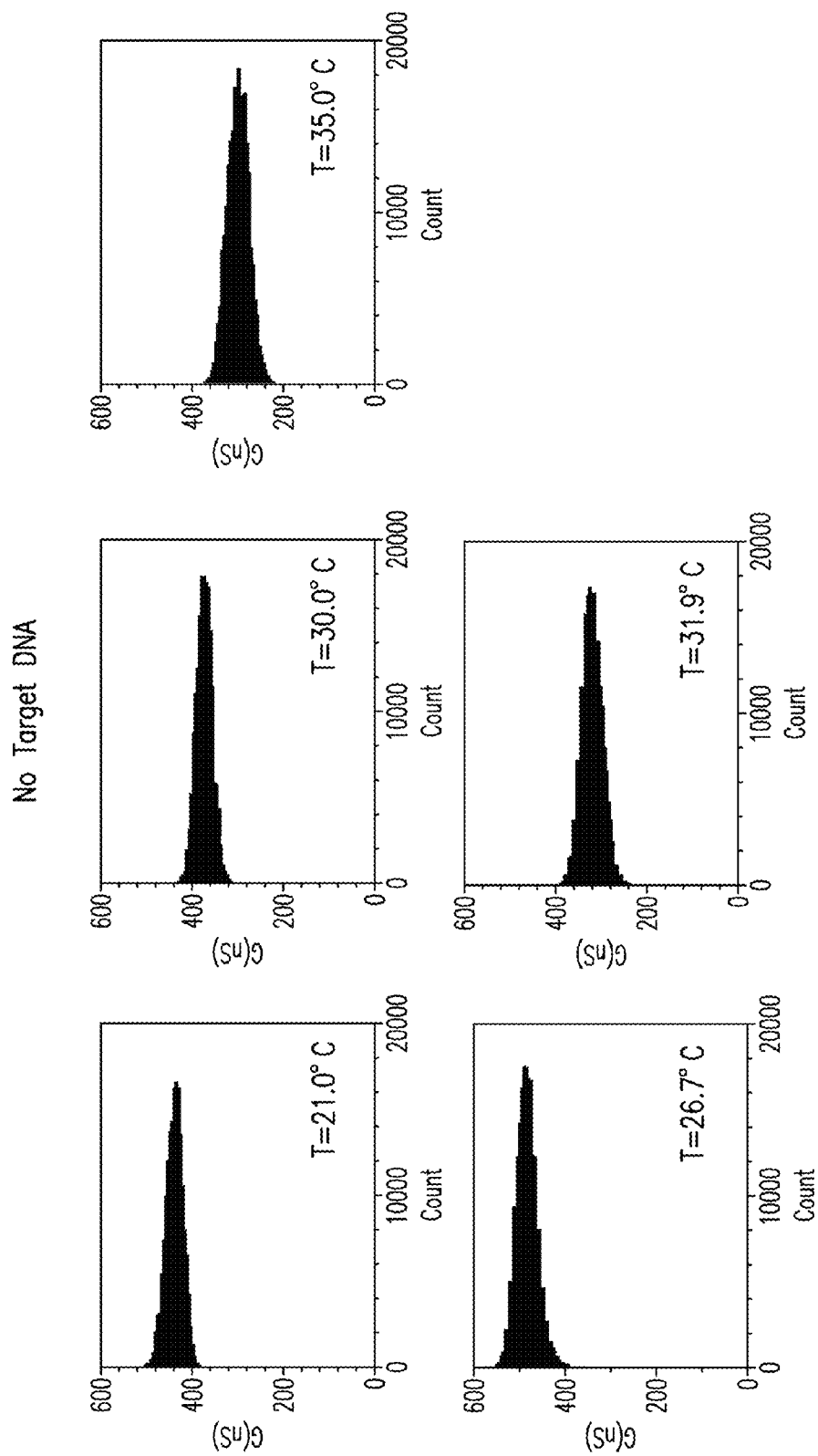

In some embodiments, the point-functionalized devices in accordance with the disclosed subject matter can be used to study the kinetics and thermodynamics of DNA hybridization for two different 10 mer duplex DNAs with the experimental setup shown in FIG. 3e for the purpose of illustration. FIG. 3e shows the external circular heater/refrigerator used to control the temperature. Probe DNA, terminated with an amine group and a three-carbon linker at the 5' end is covalently attached to the carboxyl defect on the nanotube through a standard coupling reaction using sulfo-N-hydroxysuccinimide (sulfo-NHS) and 1-ethyl-3-(3-dimethylaminopropyl)carbodiimide (EDC). After thoroughly rinsing the device with de-ionized water, subsequent measurements are carried out in phosphate buffered saline solution (1×PBS, pH=7.4). After attaching the probe DNA to the point defect in the nanotube, the temperature is controlled with a thermal water bath (±0.1° C.). When thermal equilibrium is reached (~10 minutes), the device conductance was monitored for periods of 30 seconds. Without the presence of target DNA, the devices show no particular features in a conductance dominated by flicker (1/f) noise as shown in FIG. 4a. The intrinsic bandwidth of the device exceeds 10 kHz, but external measurement filters can be applied to reduce the bandwidth to 4 kHz for the measurements presented herein. This results in an overall input-referred noise level of ~1 nArms at 100 mV source to drain bias.

Figures 1, 4C:
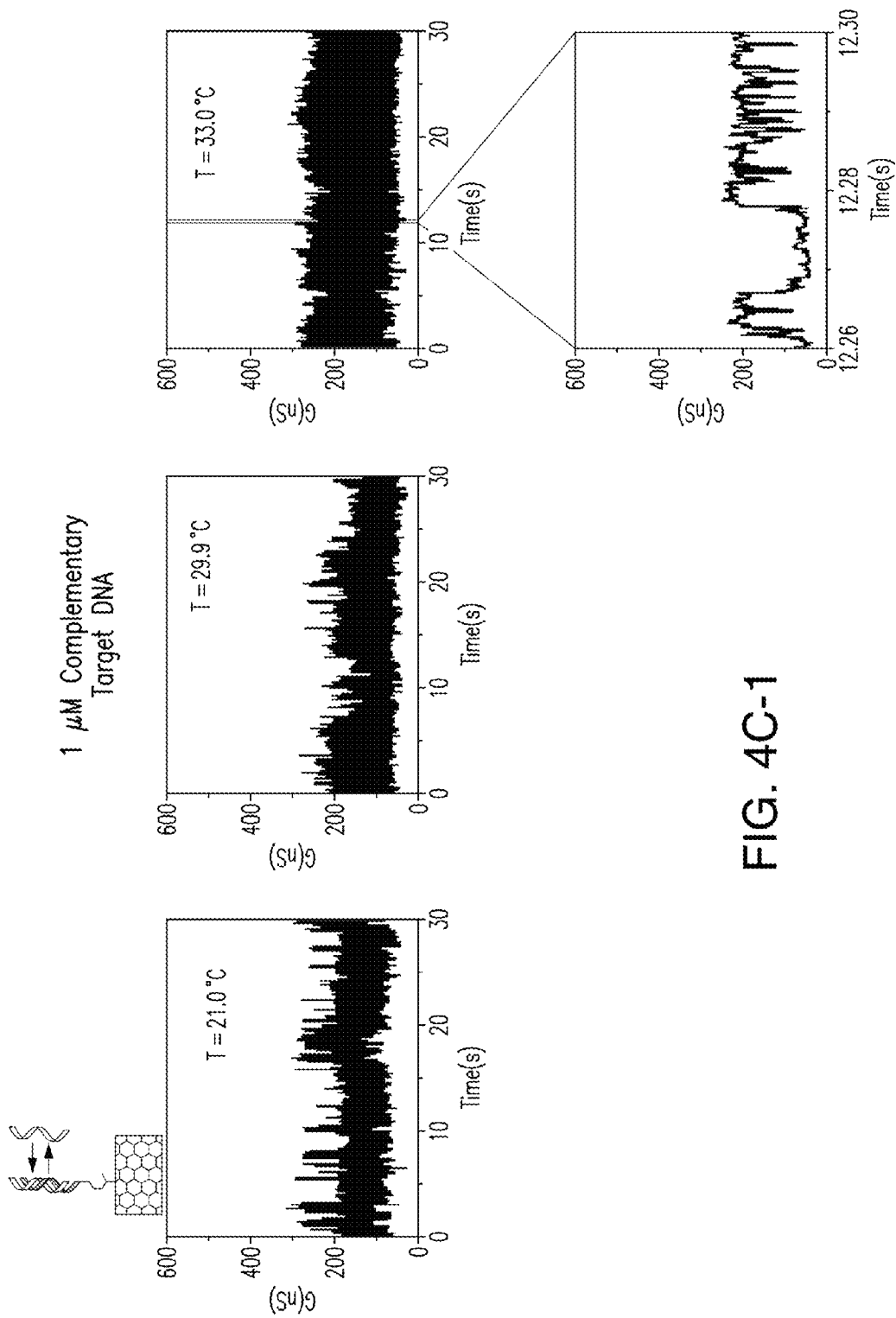
Figures 2, 4C:
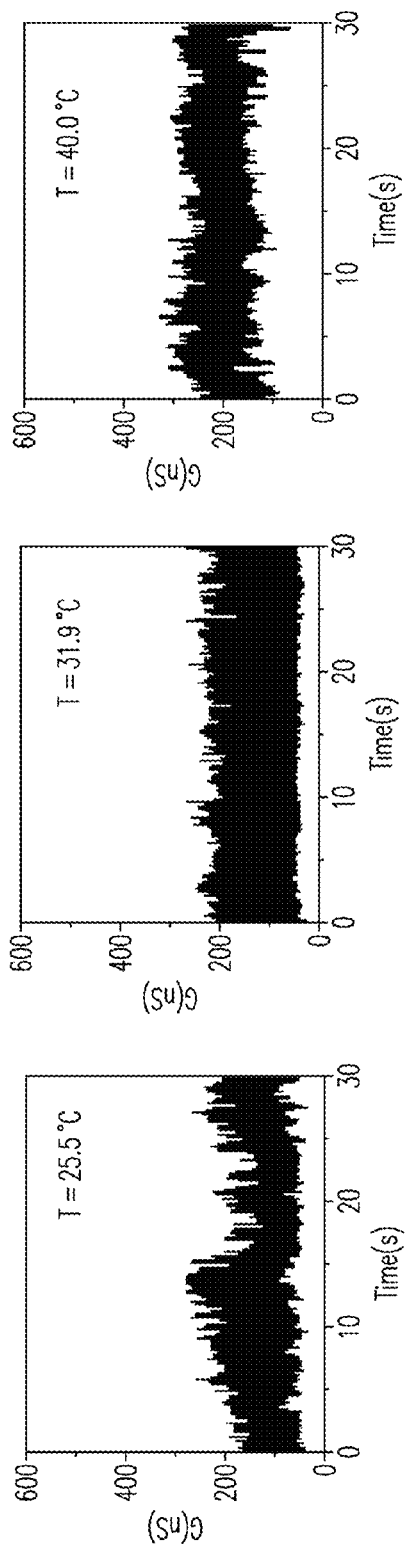

When the device is immersed in buffer containing complementary target DNA, however, large-amplitude two-level fluctuations appear as shown in FIGS. 4c-1 and 4c-2, for the purpose of illustration, with a conductance difference of approximately 60-100 nS with an SNR of better than three over the 1/f noise background for a time interval of 30 seconds, which can be improved by going to shorter time intervals. The real time conductance data of a representative device (Device 1) is shown with the probe DNA $NH_2$-5'-GGAAAAAAGG-3' (probe $A_6$) and 1 μM complementary target DNA. The two conductance states have a strong temperature dependence: the device is mostly in the low-conductance state at low temperature and in the high-conductance state both at high temperature and prior to the addition of target DNA. Around the melting temperature, the two states are similarly occupied. Due to this evident temperature correlation, a model can be proposed in which the conductance is modulated by probe-target hybridization, consistent with other observations that target DNA binding to covalently attached DNA probe reduces tube conductance due to increased scattering and charge transfer at the defect created by the target attachment. The low conductance state represents a device with duplex DNA and the high conductance state represents a device with unbound probe DNA. In principle, longer DNA strands should increase scattering further and result in larger amplitude fluctuations, but it is expected that this effect would be partially offset by Debye screening from the dissolved solution counterions. The above model is further supported by the observation that these two-level fluctuations are not observed in pristine control devices without electrochemical modification either before or after the addition of target DNA and control devices that have been linked with probe DNA with non-complementary target. Of note, there is a baseline drop in the conductance after DNA target is added, which can be attributed to non-specific adsorption.

The conductance modulation can be related to a change in the transmission probability at the defect using the Landauer-Büttiker formalism as:

$$R_{total} = R_c + \frac{h}{4e^2}\left(1 + \frac{1-T}{T}\right) \quad (1)$$

where $R_c$ is the resistance of the device before oxidation and T is the transmission probability through the defect. For this particular device, $R_c$=53 kΩ and the transmission probability changes from 0.0055 before adding DNA target to roughly 0.0018 with target; that is, when the target DNA binds, the transmission probability is modulated by a factor of three. Neither AFM nor SGM techniques have sufficient spatial resolution to determine if the change in the device happens at a single carboxylate or if only a single DNA molecule covalently attaches to the nanotube. Multiple DNA probes can be attached to the nanotube leading to multi-level fluctuation; however, because of the strong two-level fluctuations, it can be concluded that only a single DNA interaction dominates the conductance modulation and the fluctuations are fit to a two-level model.

Figure 4D:
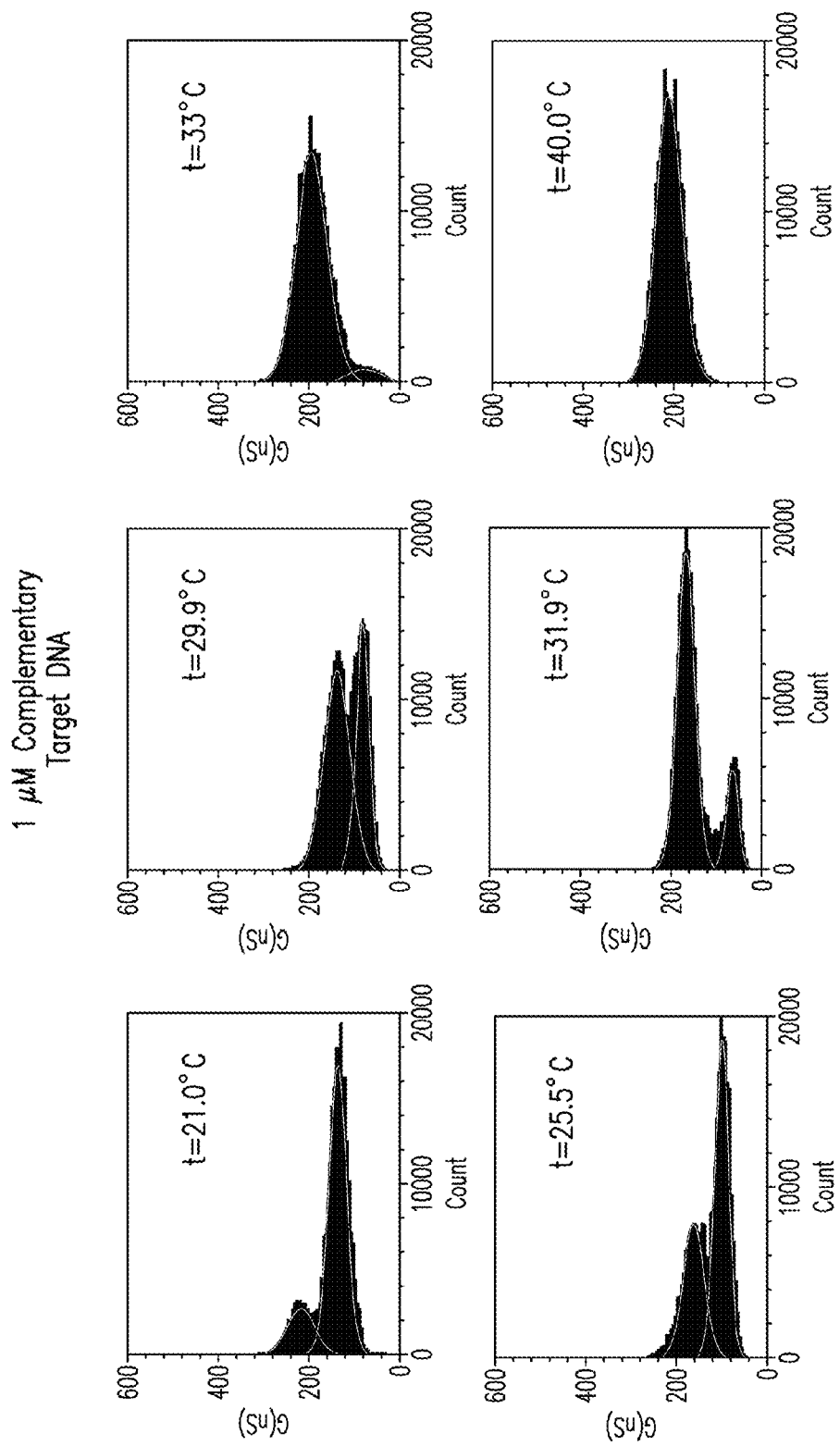
FIG. 4d is a series of conductance based-histograms for the recordings of FIG. 4c-2.
Figure 5A:
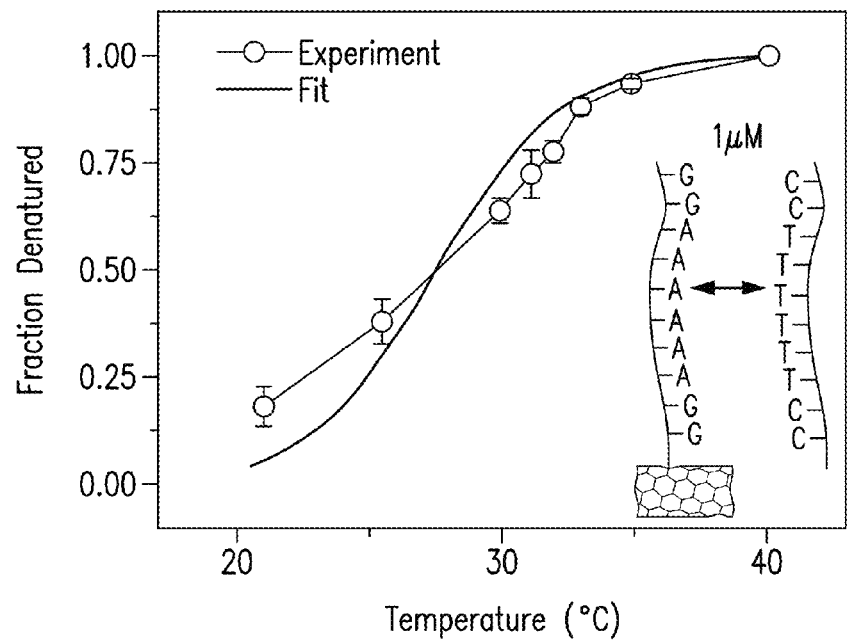
FIGS. 5a, 5b, and 5c are melting curves in accordance with some embodiments of the disclosed subject matter.

By taking the ratio of the areas under the low and high conductance state curves from the Gaussian fits in FIG. 4d, the melting curve can be obtained as shown in FIG. 5a. Assuming a two-state model where the DNA strands are either in single or in duplex form, the equilibrium constant, K, in solution is given by K=2α/(1-α)$^2$ where α is the fraction of total strand concentration C that is in duplex faun. For surface based hybridization, the equilibrium constant can be written as the Langmuir isotherm K=2α/(1-α)C. For both surface-based and solution-based hybridization, the temperature can be related to the fraction of DNA in duplex form through the thermodynamic relation −RT ln(K)=ΔH°−TΔS°. The melting temperature of the DNA duplex (where α=0.5) as measured by the nanotube ($T_m$=27.5° C.) is slightly lower and the transition is sharper compared to the free DNA ($T_m$=32.3° C.).

Figure 5B:
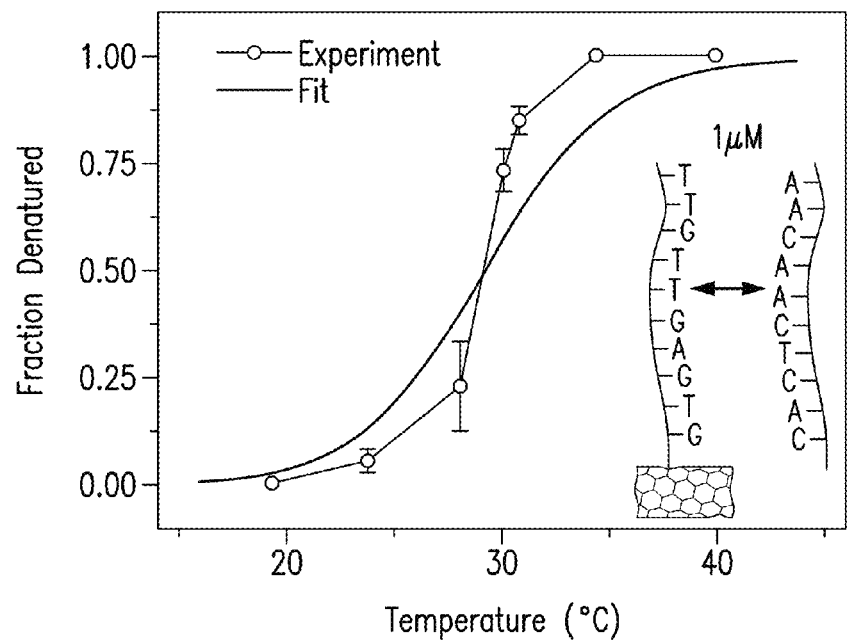
Figure 5C:
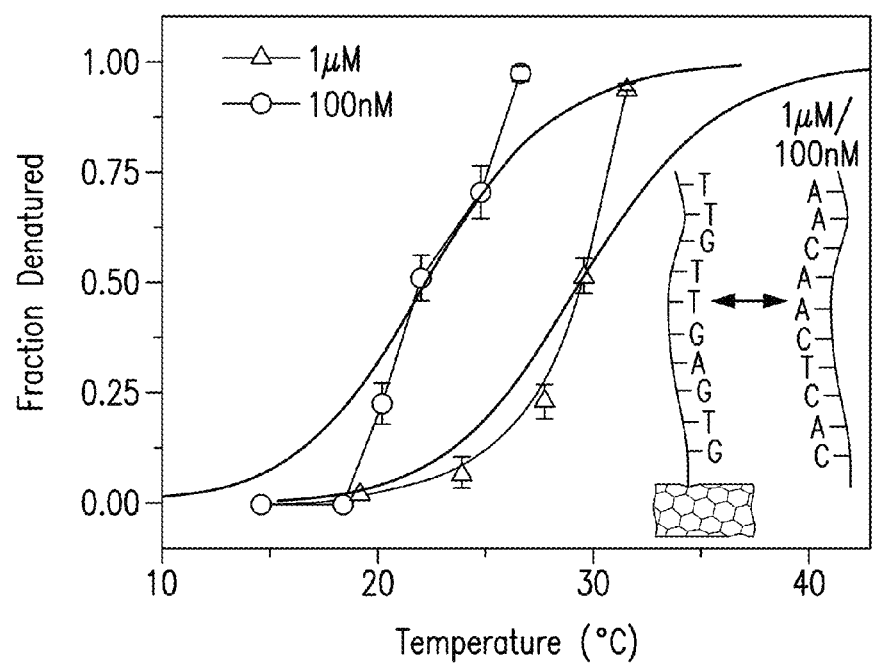

For the purpose of illustration, FIGS. 5b and 5c show the melting curves extracted for the different probe oligonucleotide $NH_2$-5'-GTGAGTTGTT-3' (probe $A_1$). Results are shown for a nanotube device (Device 2) with 1 µM complementary target concentration (FIG. 5b) and another device (Device 3) with both 1 µM and 100 nM complementary target concentrations (FIG. 5c). The lower target concentration reduces the melting temperature, similar to what has been observed in bulk solution. The thermodynamic properties for both DNA strands are summarized and compared to results with standard UV-Vis analysis in Table 1.

ments to study conformational changes in biomolecules. The lifetime in each state is extracted by exponentially fitting the dwell time histograms.

Figure 6A:
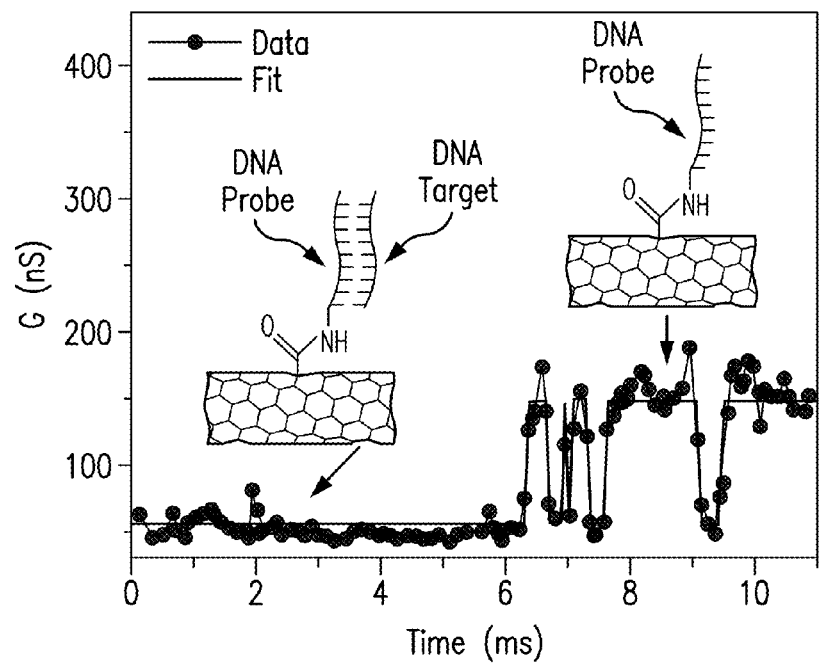
FIG. 6a is a graph of the conductance of a carbon nanotube device in accordance with some embodiments of the disclosed subject matter.
Figure 6B:
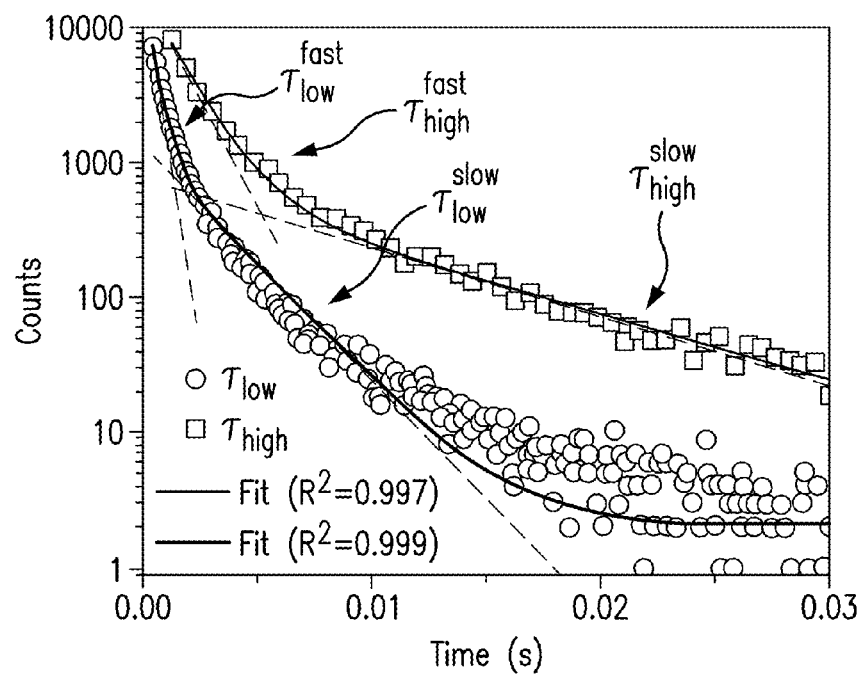
FIG. 6b is dwell time histogram of a carbon nanotube device in accordance with some embodiments of the disclosed subject matter.
Figure 6C:
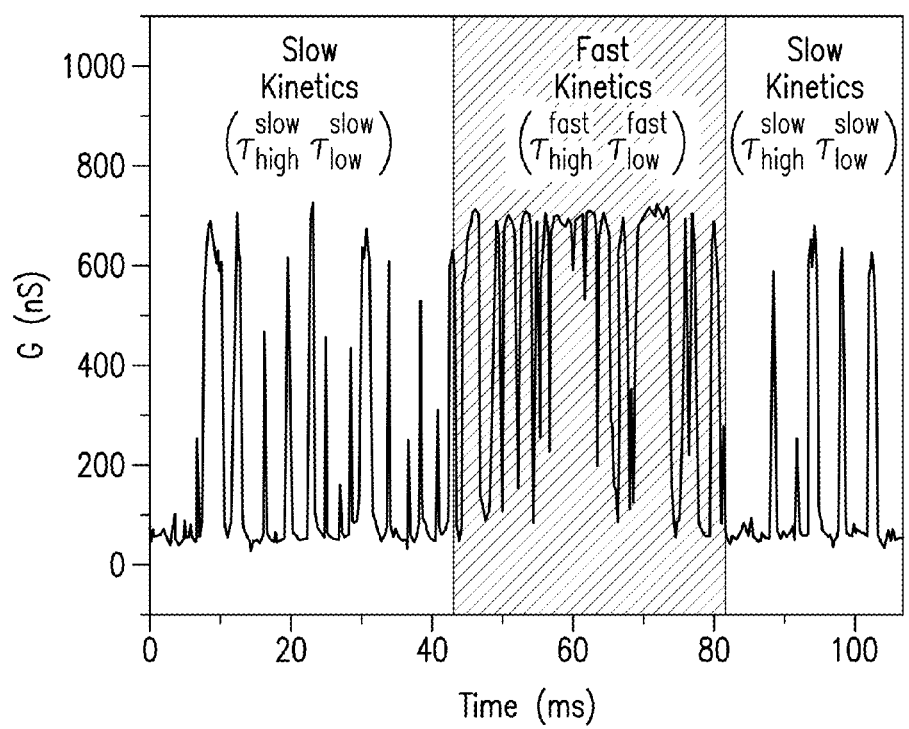
FIG. 6c is a graph of the conductance of a carbon nanotube device in accordance with some embodiments of the disclosed subject matter.
Figure 6D:
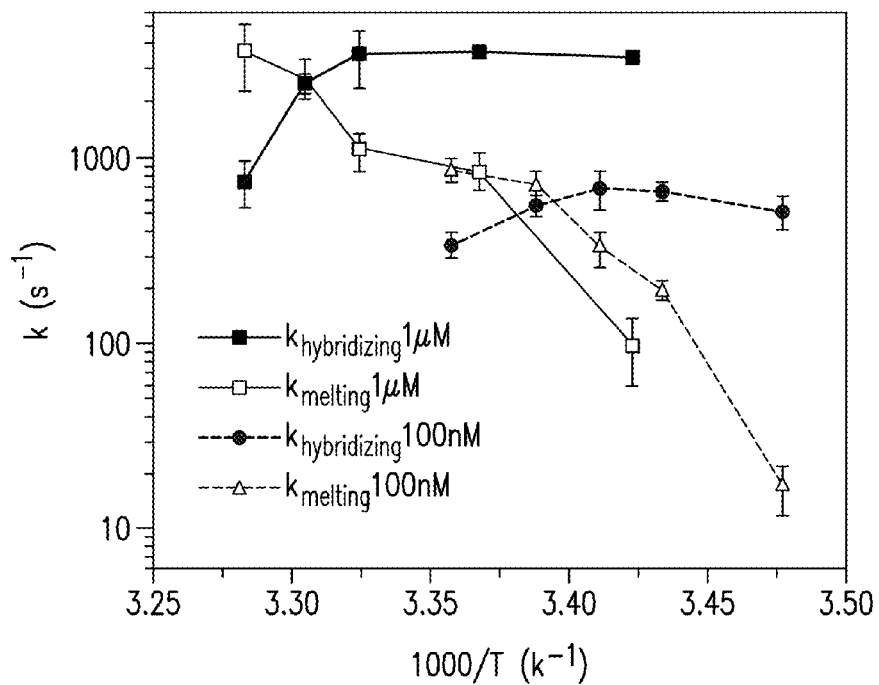
FIGS. 6d, 6e, 6f are Arrhenius plots in accordance with some embodiments of the disclosed subject matter.

From this lifetime analysis, it can be determined that the dwell time histograms can be best fit by a double exponential function with time constants, $\tau_{low}^{fast} < \tau_{low}^{slow}$ and $\tau_{high}^{fast} < \tau_{high}^{slow}$, as shown in FIG. 6b. The origin for the double exponential can be the result of two competing pathways for hybridization. Similar models have been used to describe DNA hybridization kinetics with immobilized probes on silicon or glass and how proteins find specific target sites along DNA strands. In this model, target DNA reach probe by either 3D diffusion or non-specific adsorption followed by surface diffusion. As shown in FIG. 4c, the nanotube conductance switches between two distinct kinetic modes which have different time constants. How these time constants are associated with solution-based or surface-based kinetics is determined by examining the concentration dependence of the associated dwell times. From chemical kinetics, it is expected that the solution hybridization rate ($k_{hybridization}$) will be proportional to DNA target concentration (bimolecular process) and the solution melting rate ($k_{melting}$) to be independent of concentration (unimolecular process). FIG. 6d shows the Arrhenius plot for Device 3 with 100 nM and 1 µM complementary target concentration using $k_{hybridization}=1/\tau_{high}^{fast}$ and $k_{melting}=1/\tau_{low}^{fast}$ for the 1 µM concentration and $k_{hybridization}=1/\tau_{high}^{slow}$ and $k_{melting}=1/\tau_{low}^{slow}$ for the 100 nM concentration so that the hybridizing and melting rates behave as expected based on solution ensemble experiments and as described above. It is believed that the target concentration at which $k_{hybridization}(k_{melting})$ goes from being determined by $\tau_{high}^{fast}(\tau_{low}^{fast})$ to being determined by $\tau_{high}^{slow}(\tau_{low}^{slow})$ depends on the ration of one-dimensional and three-dimensional diffusion rates and the concentration dependence of the surface-based hybridization and melting rates.

Figure 6E:
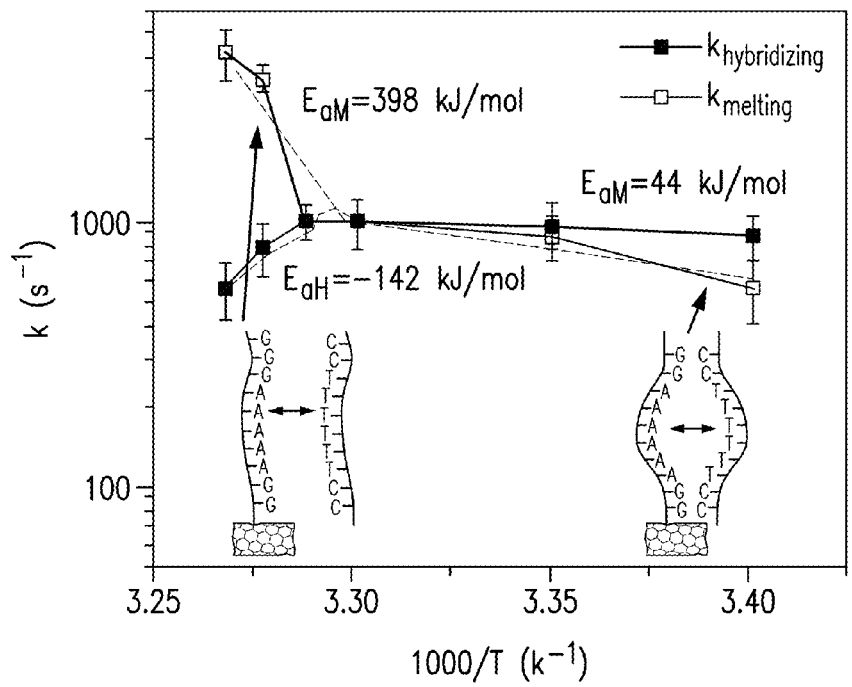
Figure 6F:
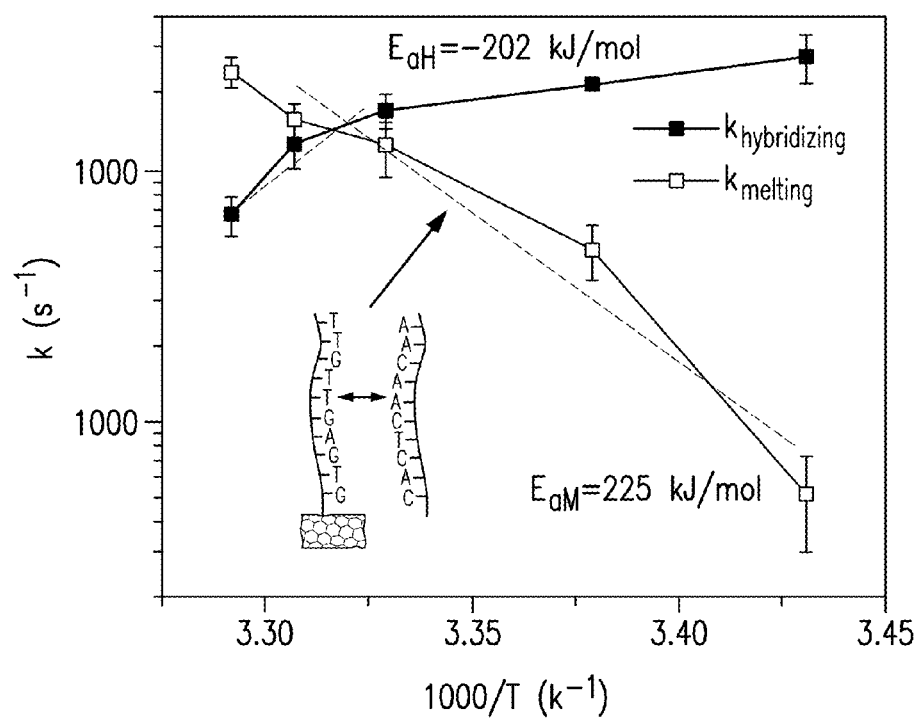

For the purpose of illustration, Arrhenius plots for $k_{hybridization}$ and $k_{melting}$ at 1 µM for Devices 1(probe $A_6$) and 2(probe $A_1$) are presented in FIGS. 6e and 6f, respectively. The Arrhenius plot of Device 2(FIG. 6f) looks very similar to ones for DNA duplex kinetics studied with DNA hairpins. The melting rates ($k_{melting}$) follow Arrhenius-like behavior and are very dependent on temperature while the hybridization rates ($k_{hybridizing}$) have anti-Arrhenius behavior and are only slightly temperature-dependent. This anti-Arrhenius behavior yields a negative activation energy, which implies

TABLE 1

| DNA | | Method | ΔH° (kJ/mol) | ΔS° (J/Kmol) | Tm(° C.) (1 µM) | Ea(kJ/mol) (hybridizing) | Ea(kJ/mol) (melting) |
|---|---|---|---|---|---|---|---|
| Probe($A_6$): | $NH_2$-5'-GGAAAAAAGG-3' | Solution | 384 | 1134 | 32.3 | — | — |
| Target: | 3'-CCTTTTTTCC-5' | Nanotube | 313 | 923 | 27.5 | −142 | 44/398 |
| Probe($A_1$): | $NH_2$-5'-GTGAGTTGTT-3' | Solution | 357 | 1026 | 36.2 | — | — |
| Target: | 3'-CACTCAACAA-5' | Nanotube | 239 | 674 | 29.4 | −202 | 225 |

In order to study the kinetics of DNA hybridization and obtain further insight into the thermodynamics observed through time averaging of a single molecule system, as shown in FIG. 6a for the purpose of illustration, the dwell times are extracted in the high ($\tau_{high}$) and low states ($\tau_{low}$) in the presence of flicker noise by idealizing the transitions using a hidden Markov model (incorporated in the vbFRET software package), which has been used in smFRET experithat the reaction rate decreases with increasing temperature and the free energy barrier arises from a significant loss of entropy. The slight curvature in the Arrhenius plot has also been observed with DNA hairpin hybridization and protein folding and is attributed to a change in the rate limiting portion of the reaction as a function of temperature, because of a significant temperature dependence in either the activation entropy or enthalpy.

The Arrhenius plot of Device 1 (FIG. 6e) shows a remarkably different behavior for $k_{melting}$, with a sharp change in activation energy around the melting temperature. At temperatures less than the melting temperature, $k_{melting}$ has a small activation energy (44 kJ/mol) that can be seen from the shallow slope in the Arrhenius plot. This can be attributed to breathing of the DNA duplex (probe $A_6$ for Device 1) which consists of six adeninethymine (AT) base pairs that are enclosed by guanine-cytosine (GC) bases. This differs from the A1 duplex (for Devices 2 and 3), which has at most two neighboring AT bases. Without being bound by theory, the fluctuations below the melting point for Device 1 could be due to bubble dynamics of the AT region.

In addition to the solution and surface modes, occasional several-second long non-ergodic time intervals when the fluctuations stop are observed, which translates into long tails in the dwell time histograms. This behavior could be due to reversible states in which the DNA complex can adhere to the nanotube surface in a conformation that impedes the binding dynamics. From the dwell time histogram, the percentage of non-ergodic time intervals is estimated to be approximately 10% of the total monitored time.

Thus, as described above, one embodiment of the disclosed subject matter is a single-molecule bioanalytical system that is capable of detecting molecules and probing molecular dynamics at microsecond time scales. This method can be used in any applicable applications including, but not limited to, single molecule studies with fast time resolution, such as label free single-nucleotide polymorphism (SNP) detection and sequencing-by-synthesis (SBS), and single molecule studies of protein folding, protein conformational changes, and/or protein or biomolecule rotation on tether) and enzymatic activity. Other applications can include the study of biomolecular processes, ultrafast chemical reaction dynamics, and chemical kinetics studies. Further applications can include identification and quantification of target DNA, RNA or protein molecules in solution. These devices can be incorporated on active substrates with integrated measurement electronics to reduce both parasitic impedances and measurement noise in order to probe kinetics at even higher rates and SNR, as described below.

Figure 7A:
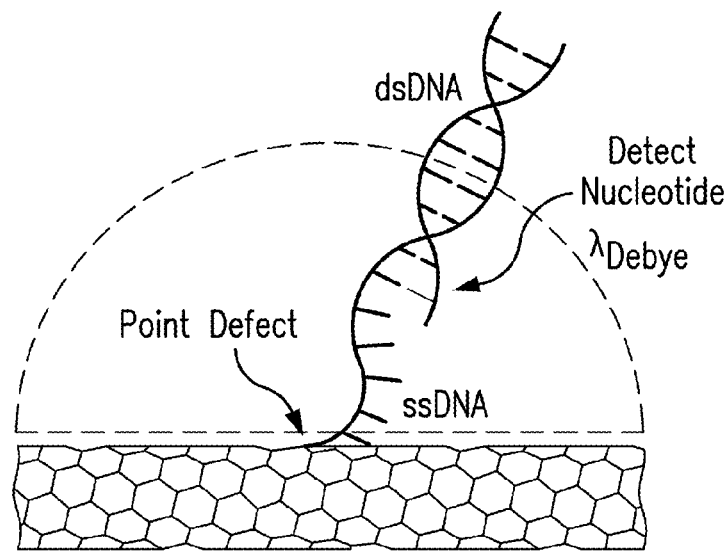
FIGS. 7a and 7b are diagrams of carbon nanotubes after introduction of a target entity in accordance with some embodiments of the disclosed subject matter.

In accordance with one embodiment of the disclosed subject matter, for SBS applications, it should be possible to observe conductance with the incorporation of new nucleotides to a probe tethered to the CNT, as shown in FIG. 7a. A challenge is the Debye length screening of the additional charge of the nucleotide as it is being incorporated. The conductance of the CNT is dominated by the defect created by the charge immobilization process. As described above, the conductance modulation can be related to a change in the transmission probability at the defect using the Landauer-Büttiker formalism. Typically $R_c$ is on the order of tens of kOhms with typical T values of less than 0.01 but is strongly modulated by charge within a Debye length of this point defect as shown in FIG. 7a.

Furthermore, DNA Polymerase or RNA Polymerase can be tethered directly to the carbon nanotube point defect. Synthesis of DNA or RNA can cause conformational changes to the polymerase. The conformational changes can modulate the local charge density around the point defect and thus can be detectable. Additionally, the change in local charge density, due at least in part to the additional charge of the nucleotide that has been incorporated in a synthesized sequence by the polymerase, can be detected.

Figure 12:
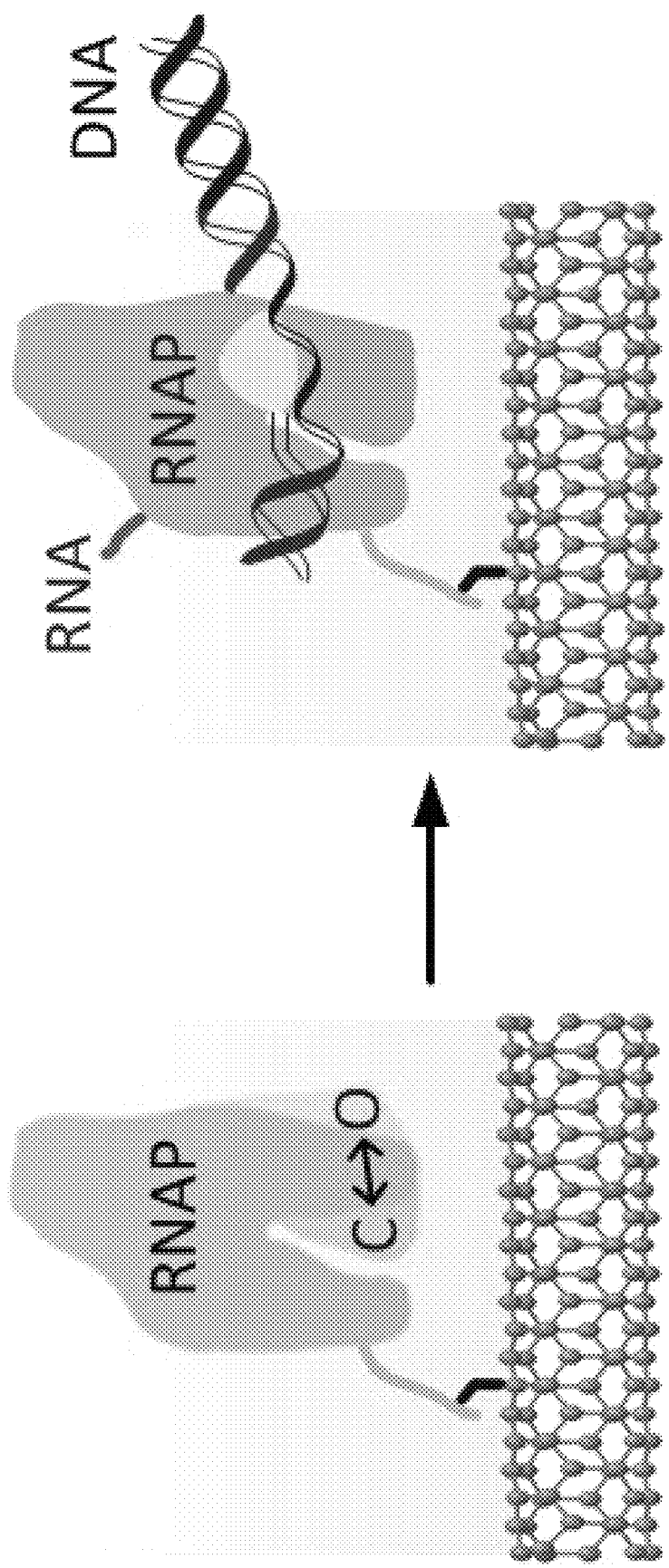
FIG. 12 is a diagram of another exemplary carbon nanotube in accordance with some embodiments of the disclosed subject matter.

For purpose of illustration and not limitation, FIG. 12 is a diagram of an alternative embodiment of a carbon nanotube in accordance with the disclosed subject matter. The carbon nanotube has a probe entity, embodied herein as a probe protein, attached thereto. For example and without limitation, and as embodied herein, the protein can be an enzyme, such as RNA Polymerase or DNA Polymerase. The probe entity can be attached to the carbon nanotube by applying a point defect to the carbon nanotube, as described further herein. The carbon nanotube shown in FIG. 12 defines a first state of the carbon nanotube.

The carbon nanotube can be introduced to a target entity to define a second state of the carbon nanotube. For the purpose of illustration and not limitation, FIG. 12 illustrates a carbon nanotube having a probe protein, embodied herein as RNA Polymerase, attached thereto at a point defect after introduction to a target entity, embodied herein as newly incorporated nucleotides in a synthesized sequence. In accordance with the disclosed subject matter, the electrical conductance of the carbon nanotube in the first and second states can be compared to detect the presence of the target entity, as described herein.

Alternatively, the probe entity can be an aptamer, and the target entity can be a protein that can bind to the aptamer. Additionally or alternatively, the probe entity can be any suitable probe protein, and the target entity can be a target protein that can bind to the probe protein.

Figure 8A:
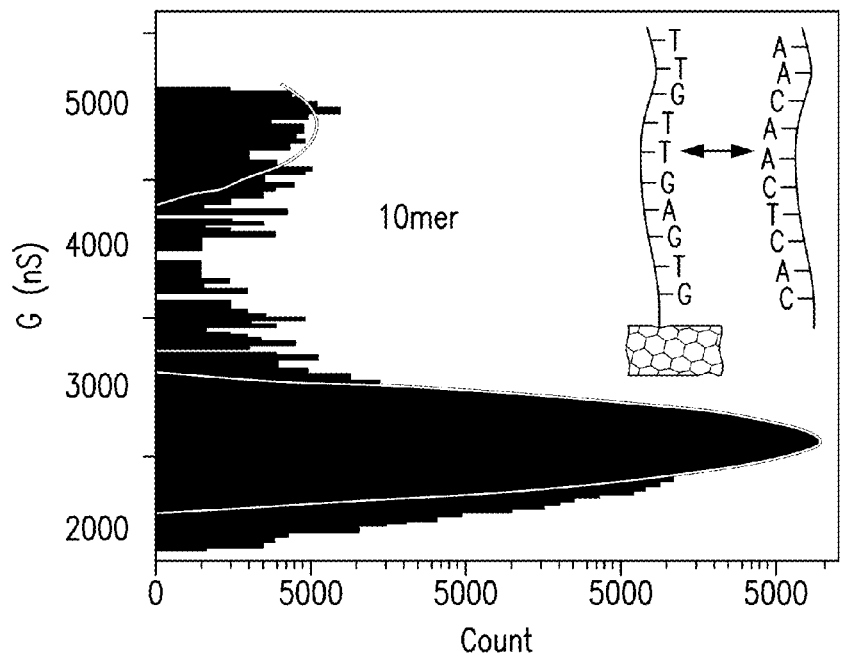
FIGS. 8a, 8b, and 8c are histograms of the conductance of carbon nanotube devices in accordance with some embodiments of the disclosed subject matter
Figure 8B:
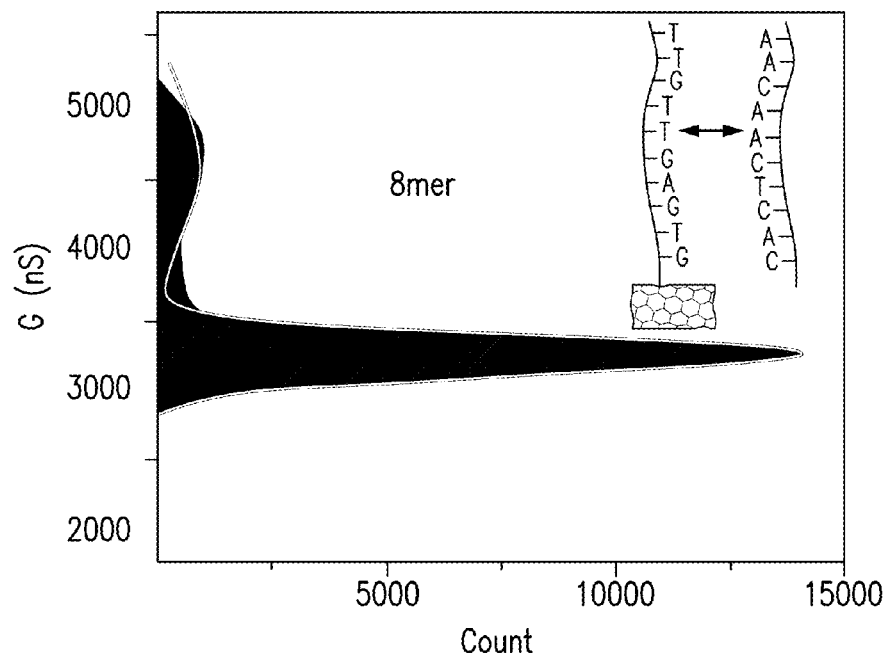
Figure 8C:
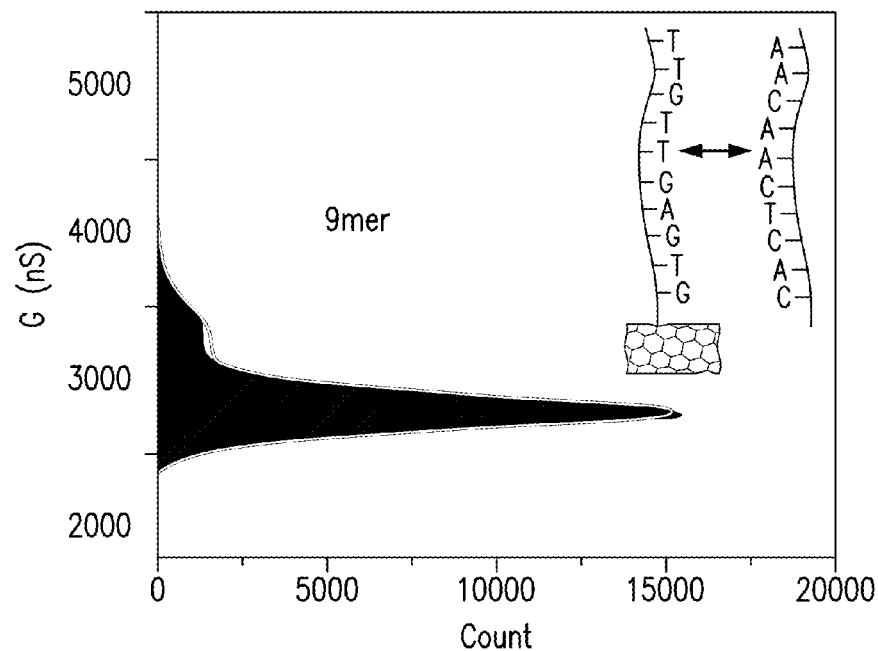
Figure 8D:
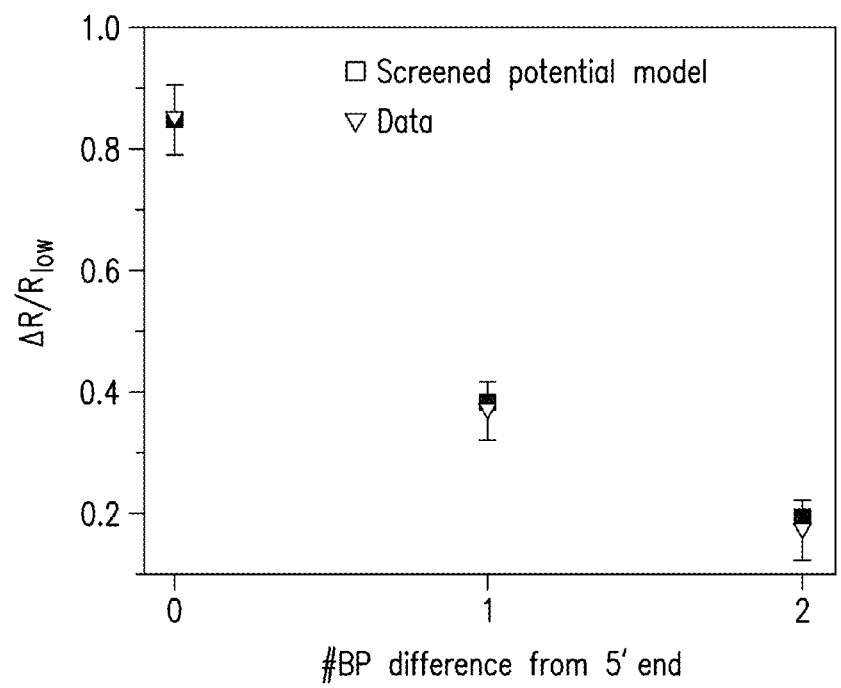
FIG. 8d is a graph of the resistance amplitude vs. target length in accordance with some embodiments of the disclosed subject matter.
Figure 8E:
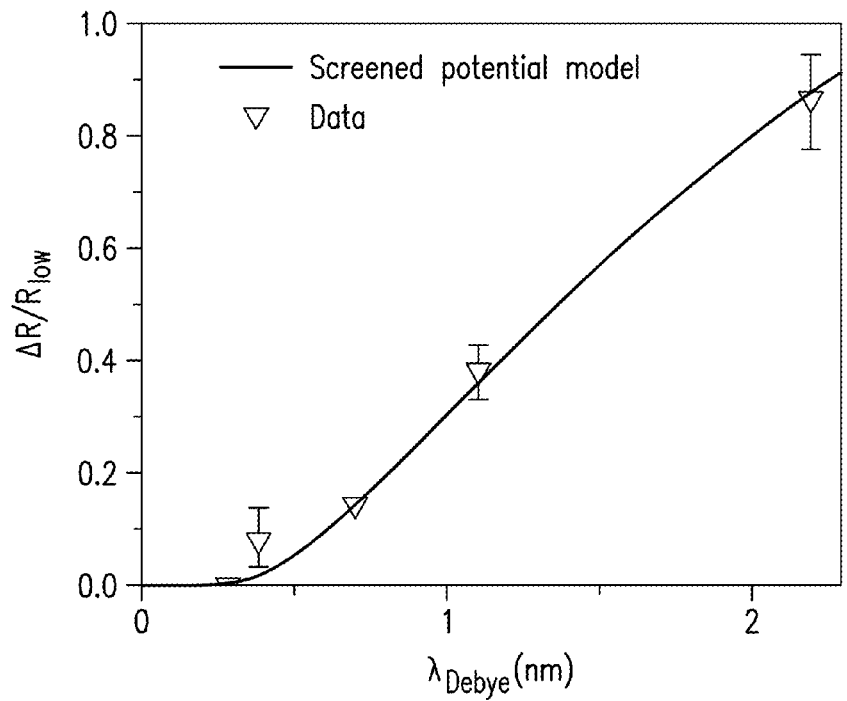
FIG. 8e is a graph of amplitude of the conductance fluctuations as a function of Debye length in accordance with some embodiments of the disclosed subject matter.
Figure 8F:
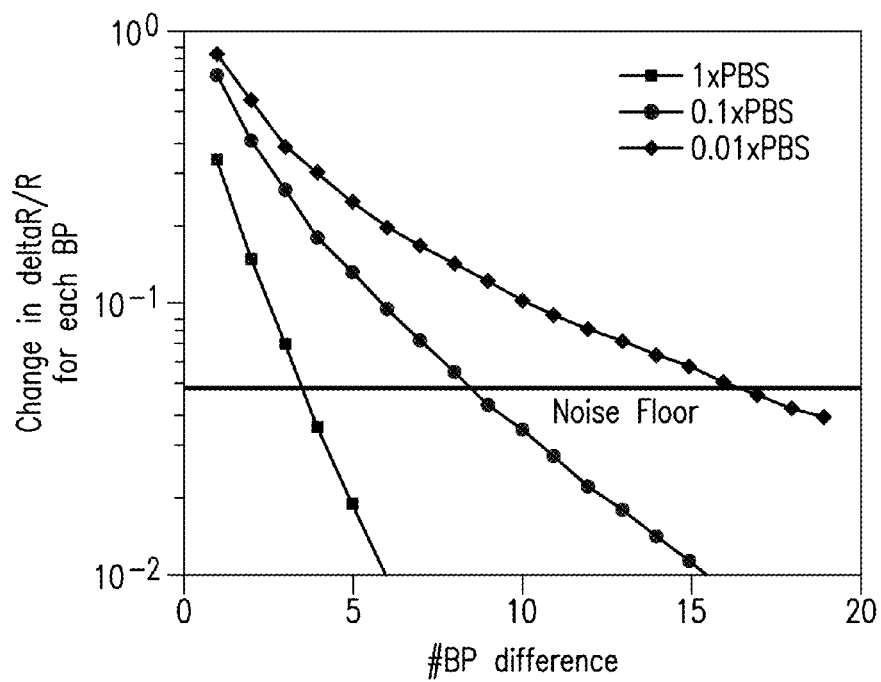
FIG. 8f is a graph of the predicted sensitivity to base-pair incorporation as a function of buffer incorporation in accordance with some embodiments of the disclosed subject matter.

To understand the signal levels (in the form of a resistance change in the CNT) that result from the charge associated with incorporating a single nucleotide, measurements were made employing a 10 mer probe, covalently attached at the 5' end to the nanotube and hybridized to targets of varying length, in which the distance of the 3' end of the target to the nanotube was varied. Given that these probe lengths are comparable to the persistence length of ssDNA, the picture is as shown in FIG. 7a. FIG. 8 shows the results of these measurements. FIGS. 8a-c are histograms of the two level conductance fluctuations that result from the binding and melting of targets of different length at a temperature of 17° C., lower than the melting temperature. The resistance amplitude that results from these different target lengths is plotted in FIG. 8d as a function of distance of the 3'-end of the target to the nanotube for a fixed buffer (1× PBS). The results follow from simple Debye length screening α

$$e^{\frac{-r}{\lambda_d}}$$

where is the Debye length. FIG. 8e, shows measurements of the amplitude of the conductance fluctuations as a function of Debye length for the 8 mer target; the Debye length is varied by varying the buffer concentration. These measured results are similar to predictions from simulations, as shown in FIG. 8e.

Figure 7B:
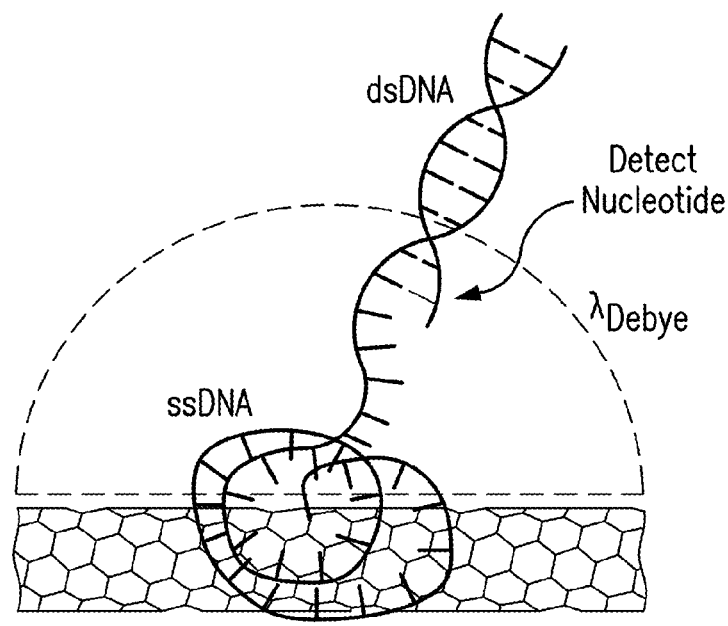

Based on these Debye-length simulations, FIG. 8 shows the limits of detection for various buffer concentrations. At 0.01× PBS, it can be expected to detect out to 18 bases (~6 nm) from the CNT. For SBS applications, nucleotide incorporation of much longer probe molecules will need to be detected. Such detection is possible because of the relatively short persistence length of ssDNA (~3 nm or 9 bases). As a result for longer sequences, the DNA is more likely to appear as shown in FIG. 7b with the coiled up ssDNA near the vicinity of the tube. This will also place the additional charge of added nucleotides within a Debye length of the resistance-modulating defect in the CNT.

The gain of the CNT sensor can be tuned by the amount of bias applied between the electrolyte and the tube, which varies the transmission coefficient T of the point defect. This bias can be applied through a platinum wire in a pseudo-reference configuration or using an Ag/AgCl electrode both in a pseudo-reference configuration or a potentiostat configuration (using both the platinum and Ag/AgCl electrode in a feedback system). The choice of electrode does not affect the results. Advantages of a Pt electrode include that it can withstand a harsh electrochemical environment and that it can be easily cleaned.

Cleavable fluorescent nucleotide reversible terminators (NRT) for SBS are known. In addition, 3'-O-modified NRTs solve the homopolymer sequencing problem in conventional pyrosequencing as is known in the art.

Figure 9:
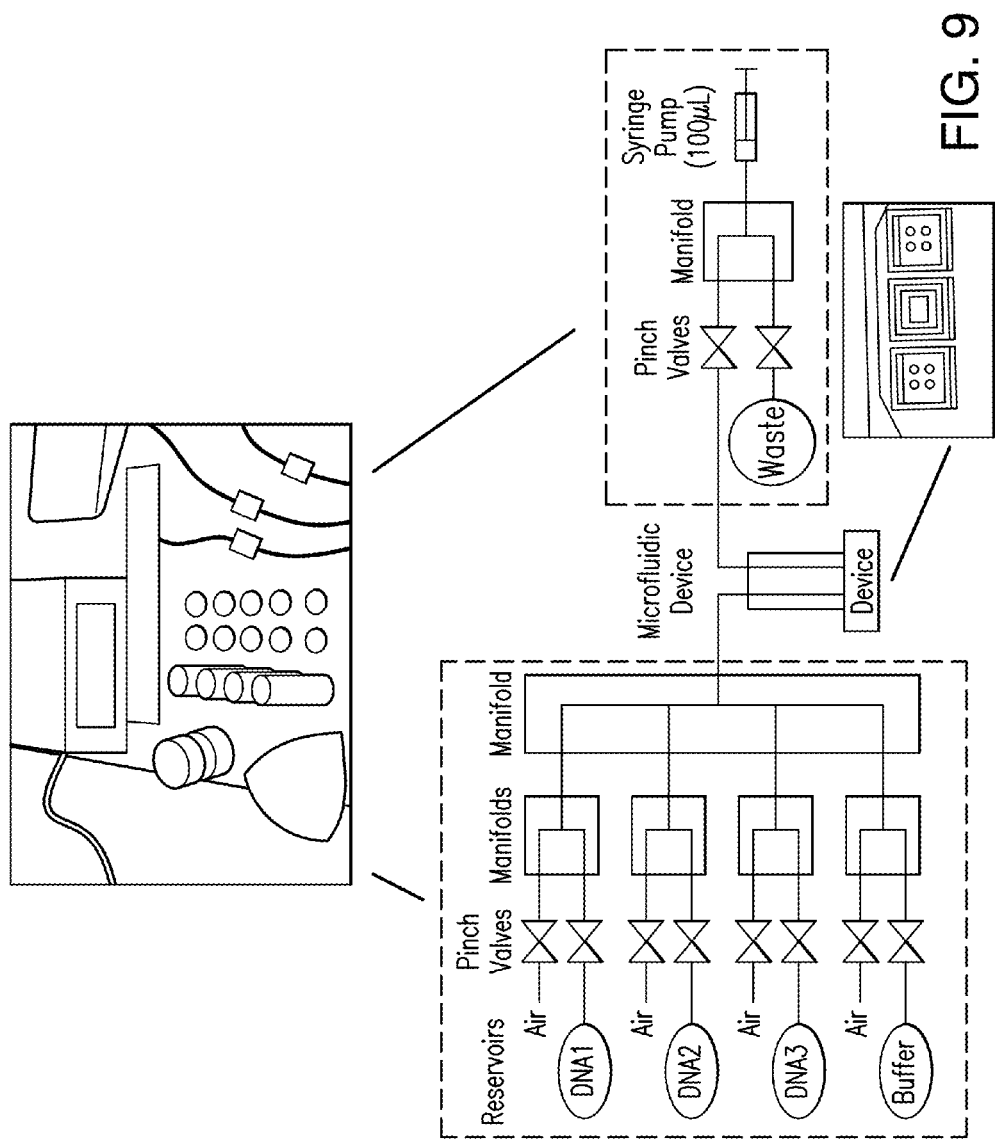
FIG. 9 is a photograph and schematic of a microfluidic delivery system in accordance with some embodiments of the disclosed subject matter.

In accordance with one aspect of the disclosed subject matter, a microfluidic delivery system, required for SBS, is shown in FIG. 9. This system interfaces with the CNT sensors through channels in polydimethysiloxane (PDMS). The system allows controlled volume as small at 20μL to be delivered to the chip with air gaps in the tubing introduced to separate sample volumes. The entire system is computer controlled.

3'-O-modified NRTs, such as 3'-Oazidomethyl-dNTPs (3'—O—N3-dNTPs), are used for single molecule SBS on the point-functionalized CNTs. The four NRTs are added one at a time through the microfluidic delivery system to the template and primer moiety for polymerase incorporation, similar to performing pyrosequencing. Only the matched NRT are incorporated into the growing DNA strand, which produces a unique electronic signature for determining the incorporated NRT. After detection, the 3'-O-azidomethyl group is cleaved by established protocol using aqueous Tris(2-carboxy-ethyl)phosphine (TCEP) solution to continue sequence detection.

Figure 10:
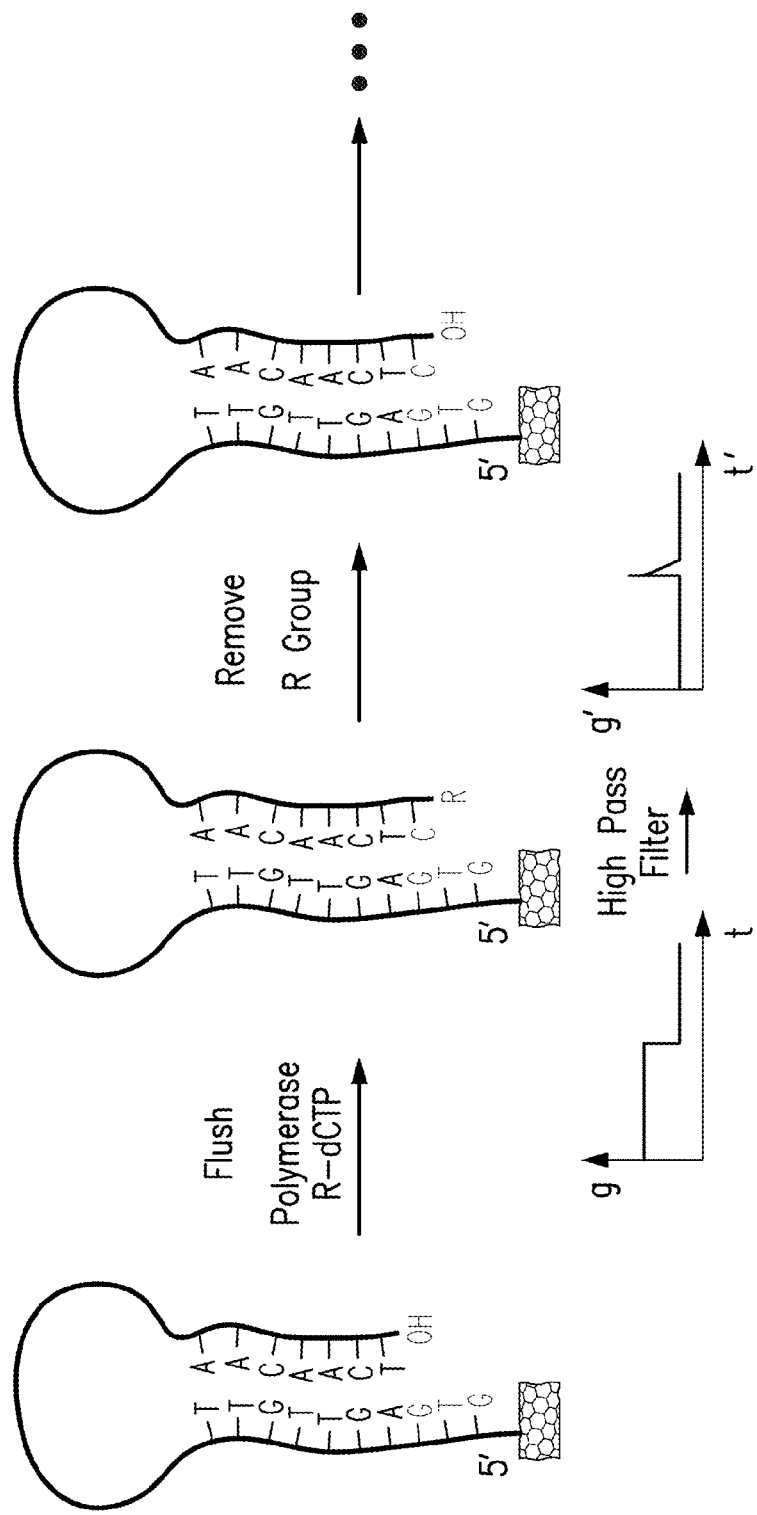
FIG. 10 is a diagram of a SBS protocol in accordance with some embodiments of the disclosed subject matter.

An exemplary sequencing scheme is shown in FIG. 10 for the purpose of illustration and not limitation. First, a looped DNA moiety is covalently attached on the CNT at the point defect site. Next the NRT with a C base that is complementary to the base G in the template is added. Electronic detection is performed to determine the single nucleotide incorporation event. The sequencing process continues following the removing of the 3'—OH blocking group. Steps in the resistance (or conductance) of the tube are detected on incorporation as shown in FIG. 10. High-pass filtering this signal as a function of time (as shown in FIG. 10) can allow further reduction of the effects of flicker noise and improve SNR as described further below. These use relatively low concentration delivery of NRTs to allow time for the CNT to equilibrate to its new aqueous environment before the NRT incorporation event occurs.

Figure 11A:
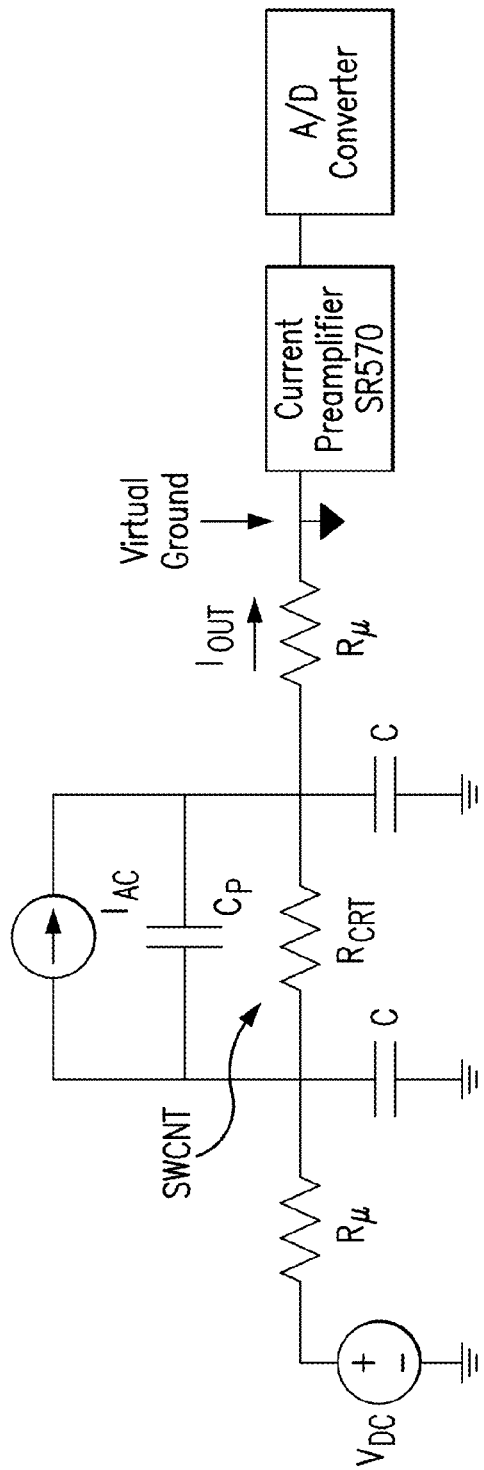
FIG. 11a is a schematic of measurement electronics in accordance with some embodiments of the disclosed subject matter.

Fluorescence-based techniques can be easily scaled up to additional channels by relying on large-pixel imaging chips for sensing. In the case of label free sensing, scale up requires integrated electronics to allow each sensor to be addressed and measured. In addition to the advantages of simpler sample preparation and measurement equipment, one of the potential advantages that direct electrical sensing has over fluorescence-based approaches is one of noise-limited bandwidth. The equivalent small-signal model of the nanotube devices with off-chip electronics is shown in FIG. 11a. Device bandwidth is limited most strongly by parasitics associated with the sensor itself. The dominant pole is given by $$f_1 = \frac{1}{2\pi} \frac{\frac{2}{R_{CNT}} + \frac{1}{R_p}}{2C + C_p}.$$

Figure 11B:
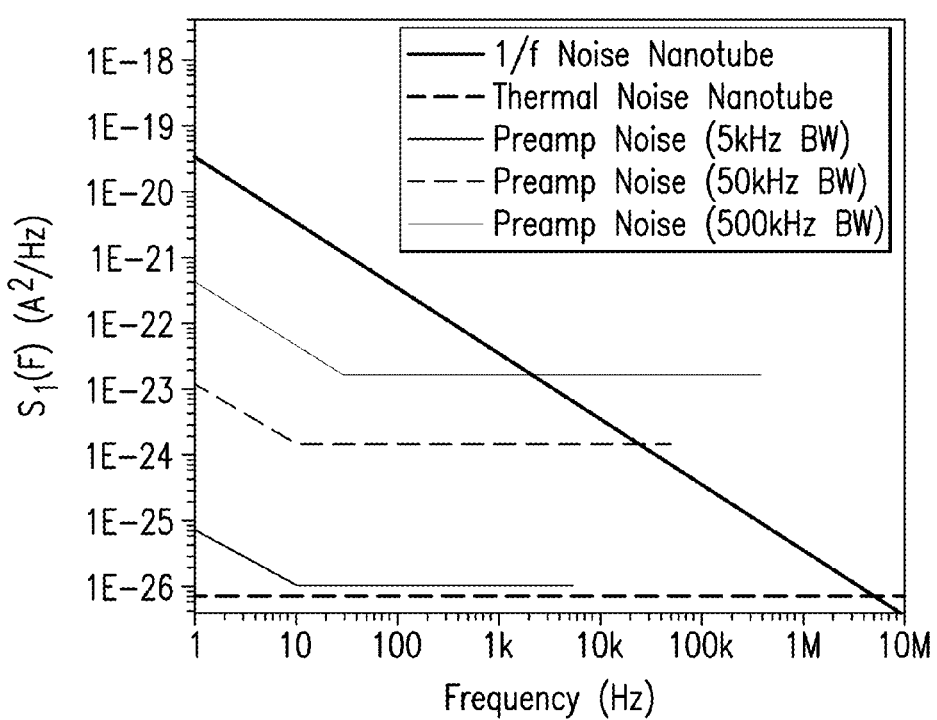
FIG. 11b is a graph of the noise spectra of a nanotube device in accordance with some embodiments of the disclosed subject matter.

Current values are $R_p \sim 5$ k$\Omega$, $C_p \sim 2.1$ nF, C~500 pF and $R_{CNT} \sim 20$ M$\Omega$, giving $f_1 \sim 10$ kHz. The bandwidth of the device can easily be improved by reducing these parasitics. This reduction can be accomplished by the use of an insulating substrate to reduce C, better passivation of the electrodes (with an oxide or resist) and reduction of their size to reduce $C_p$ and use of a different contact metal to reduce the series resistance $R_p$. With these improvements, bandwidth can be easily improved to 1 MHz or more. As shown in FIG. 11b, 1/f noise can be expected to dominate noise performance out to 1 MHz but even if no efforts are made to reduce this noise below current levels, input referred noise current will still be less than 1 nA rms.

Extensive custom integrated circuits can be used for the measurement of random telegraph noise in CMOS technologies, which can easily adapted to provide the measurement capabilities for the disclosed subject matter. Nanotubes can be transferred to these substrates lithographically or with dielectrophoretic techniques, as is known in the art. The microfluidic assembly of FIG. 9 can be scaled up to be able to support multiple fluidic delivery channels. The chip can perform amplification and data conversion, presenting real-time results in digital form.

This additional bandwidth can allow performance of the electronic NRT incorporation detection in a narrow-band manner. NRT incorporation itself can be expected to be very fast (on the order of nanoseconds), which can allow high-pass filtering of the conductance signal from the CNT up to very close to the measurement bandwidth, filtering out most of the 1/f noise and improving SNR performance. This can allow measurement of the time for NRT incorporation, which is different for the different bases, which provides a mechanism for real-time SBS.

EXAMPLES

Carbon Nanotube Device Fabrication

The catalyst solution for nanotube growth is composed of p-methyl methylacetoxy calix[6]arene (MC6, Tokuyama Corp.) and Fe(III) acetylacetonate (Fe(Acac)$_3$, Aldrich) in monochlorobenzene. A solution of 1.0 Wt % MC6 and 0.1 Wt % Fe(Acac)$_3$ is brushed onto one edge of a piranha-cleaned silicon dioxide substrate (300 nm SiO$_2$) and then subjected to a pre-heated (500° C.) furnace for 10 minutes in air to remove the resist. After flushing the system with argon at the same temperature for 10 minutes, the temperature is ramped to 750° C. and connected to the reducing gases of argon and hydrogen (642 sccm and 115 sccm, respectively) to activate the iron nanoparticles for one hour. Carbon nanotubes are then grown at 880° C. for one hour by a chemical vapor deposition (CVD) process from the iron nanoparticles using ethanol as the carbon source. The flow rates for growth are 138 sccm for argon and 18 sccm for hydrogen. In general, the nanotubes grown are several millimeters long and have a spacing of approximately 50 μm.

For device fabrication, nanotubes are grown on degenerately doped silicon substrates (ρ=0.01 Ωcm) with a 300 nm thermally grown SiO$_2$ layer. Electrodes to the nanotubes are defined using optical lithography in a bilayer (120 nm LORIA/1.3μm Shipley S1813) resist, followed by electron beam evaporation of a 75 nm titanium film and lift off in PG Remover. Scanning electron microscopy (SEM) and atomic force microscopy (AFM) are used to locate the nanotubes relative to alignment marks and electrodes on the substrate and to measure their diameter (only tubes with a diameter less than 2 nm are chosen). Afterwards, another lithography procedure can be used to cover a selected nanotube followed by an oxygen plasma etch (Technics Series 800 RIE machine, 50 W RF power, oxygen 250 mTorr for 10 s) to remove other nanotubes. This etching procedure guarantees that only a single tube bridges the electrodes and that neighboring electrodes are electrically isolated. After fabrication, the substrates are annealed in forming gas (a mixture of hydrogen/argon) for at least two hours at 400° C. to remove the resist residue completely.

Measurement Instrumentation and Carbon Nanotube Device Oxidation

After wire-bonding the chips to 44-pin J-leaded chip carriers (Chelsea Technology), the wirebonds are electrically and mechanically insulated by standard epoxy (EPO-TEK GE 120 and EPO-TEK 302-3M for damming and filling). A small glass tube is fixed on top of the epoxy to create a 3-ml cavity for the aqueous experiments. A platinum wire in a pseudo-reference configuration is used to modulate the liquid gate potential while the back gate is held at zero potential. The experiment was also run with an Ag/AgCl electrode both in a pseudo-reference configuration and a potentiostat configuration (using both the platinum and Ag/AgCl electrode in a feedback system) and the choice of electrode does not affect the results. Some advantages of using a Pt electrode include that is that it can withstand the harsh electrochemical environment and that it can be easily cleaned between experiments by grinding away the outer layer with fine sandpaper and then rinsing it with de-ionized water.

For the conductance plots as a function of gate voltage, an Agilent 4155C Semiconductor Parameter Analyzer was used to sweep the electrolyte gate while monitoring the conductance in a two-probe configuration with 100 mV source-to-drain bias. The gate leakage is always negligible (<1 nA) with respect to the source drain current. This is a good indication that the native oxide of the titanium electrodes sufficiently reduces any electrochemical leakage currents. The real time experiments are monitored with a Labview program. A voltage source (Keithley 2400 Source Meter) is used to set the electrolyte voltage while the conductance through a selected device is monitored with a transimpedance current amplifier (Stanford Research SR570) that is sampled at either 10 kHz or 15 kHz using a NIDAQ card. The transimpedance amplifier also sets the source drain voltage to 100 mV and the bandwidth is 4 kHz (at 200 nA/V sensitivity, 10 kHz/12 dB low pass filter). Devices that have been oxidized in sulfuric acid (1 M $H_2SO_{4(aq)}$) are connected to a second voltage source that is always kept 0.4 V above the Pt potential to avoid further oxidation or accidental reduction. This allows several devices to be oxidized at once. Afterwards, the glass chamber was flushed with de-ionized water (while keeping the potential fixed) and then immersing the devices in 6.5 mM potassium permanganate ($KMnO_{4(aq)}$) for 45 s.

DNA Functionalization Using Carbon Nanotube

The carboxylate defects created in the nanotube during the oxidation process can be covalently linked to the DNA in a two-part process. First, the carboxylic acid group in the nanotube is activated for 30 minutes in MES buffered saline solution (pH=4.7, Pierce Biotechnology) with 1 mM EDC (1-Ethyl-3-[3-dimethylaminopropyl]carbodiimide Hydrochloride) and 2 mM Sulfo-NHS (N-hydroxyulfosuccinimide) (commercially available from Pierce Biotechnology). Then, the devices are rinsed with fresh buffer solution, followed by rinsing in 1× PBS buffer (pH=7.4). The devices is incubated in 2 µM single stranded probe DNA with an amine group at the 5' end in 1× PBS buffer (pH=7.4) with 1 mM EDC and 2 mM Sulfo-NHS overnight (14 h). The devices are then rinsed with de-ionized water and immersed in 1× PBS for further characterization.

Scanning Gate Microscopy of Carbon Nanotube

Scanning gate microscopy (SGM) is done with a Park Systems Corp. XE-100 AFM using a Cr/Au tip (NSC 14-Cr/Au) at room temperature. Both SGM and electron force microscopy (EFM) are done concurrently and the tip is lifted to 30 nm above the nanotube. For SGM, a small 50 mV bias is applied across the nanotube using a lock-in amplifier (Stanford Research SR830) and the tip is biased at −2 V. The device is slightly p-type and this negative bias increases the conductance through the local tip gating. Both the topography image and the SGM image are leveled but no further processing is done. The conductance of the pristine device increases by about 8% when the tip is over the Schottky barrier while the conductance of the point-functionalized device increases by more than 22% when the tip is over the defect.

While the disclosed subject matter is described herein in terms of certain exemplary embodiments, those skilled in the art will recognize that various modifications and improvements can be made to the application without departing from the scope thereof. Thus, it is intended that the present application include modifications and variations that are within the scope of the appended claims and their equivalents. Moreover, although individual features of one embodiment of the application can be discussed herein or shown in the drawings of one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the application such that the application should be recognized as also specifically directed to other embodiments having any other possible combinations. Thus, the foregoing description of specific embodiments of the application has been presented for purposes of illustration and description. It is not intended to be exhaustive or to limit the application to those embodiments disclosed.

The invention claimed is:

1. A method for single-molecule detection, comprising:
providing a carbon nanotube having a point defect formed therein and a probe entity attached to the point defect, the probe entity defining a first state of the carbon nanotube, wherein the probe entity comprises a protein;
introducing the carbon nanotube to a target entity to define a second state of the carbon nanotube, wherein the target entity comprises a target protein to bind to the protein of the probe entity;
comparing the electrical conductance of the carbon nanotube in the first and second states to detect the presence of a biomolecular entity.

2. The method of claim 1, further comprising carbon-generating the point defect in the carbon nanotube and attaching the probe entity to the carbon nanotube at the point defect.

3. The method of claim 2, wherein the point defect comprises a single carboxyl defect.

4. The method of claim 2, further comprising attaching the probe entity to the carbon nanotube via a coupling reaction.

5. The method of claim 1, wherein the probe entity comprises an enzyme.

6. The method of claim 5, wherein the enzyme comprises DNA polymerase or RNA polymerase.

7. The method of claim 6, wherein one or more conformational changes of the DNA polymerase or RNA polymerase defines the second state relative to the first state.

8. The method of claim 1, wherein the introducing further comprises introducing the carbon nanotube to the target entity in a buffer composition containing the target entity.

9. The method of claim 1, wherein the comparing further comprises comparing the electrical conductance of the carbon nanotube in the first and second states to predetermined conductance data to ascertain the identity of the target entity.

10. The method of claim 9, wherein the predetermined conductance data comprises a calibration curve.

11. The method of claim 1, wherein the carbon nanotube comprises a single-walled carbon nanotube.

12. The method of claim 1, wherein the carbon nanotube comprises a field effect transistor that provides an electronic signal for measuring the conductance in the first and second states of the carbon nanotube.

13. The method of claim 1, wherein the method is label free.

14. The method of claim 1, further comprising providing single-molecule protein folding activity of the biomolecular entity upon detecting the presence of the biomolecular entity.

15. The method of claim 14, wherein detection of biomoleculary entity is label free.

16. A system for single-molecule detection, comprising:

a carbon nanotube having a point defect formed therein and a probe entity attached to the point defect, the probe entity defining a first state of the carbon nanotube, wherein the probe entity comprises a protein;

a field effect transistor in electronic communication with the carbon nanotube; and a supply of a target entity that when introduced to the carbon nanotube defines a second state of the carbon nanotube such that the electrical conductance of the carbon nanotube in the first and second states is compared to detect the presence of a biomolecular entity, wherein the target entity comprises a target protein to bind to the protein of the probe entity.

17. The system for single-molecule detection of claim 16, further comprising a buffer composition to introduce a target nucleotide sequence to the carbon nanotube.

18. The system for single-molecule detection of claim 16, wherein the probe entity is attached to the carbon nanotube at a point defect.

19. The system for single-molecule detection of claim 16, wherein the target entity further comprises a complementary target nucleotide sequence.

* * * * *

UNITED STATES PATENT AND TRADEMARK OFFICE
CERTIFICATE OF CORRECTION

PATENT NO. : 9,625,404 B2
APPLICATION NO. : 13/801834
DATED : April 18, 2017
INVENTOR(S) : Sebastian Sorgenfrei et al.

It is certified that error appears in the above-identified patent and that said Letters Patent is hereby corrected as shown below:

In the Specification

On the second paragraph after the title Column 1, Lines 15 through 21, please enter a paragraph as follows:
STATEMENT OF GOVERNMENT INTERESTS
This invention was made with government support under grant numbers 0707748 and CHE-0641523, awarded by the National Science Foundation (NSF), grant number HG006882 awarded by the National Institute of Health (NIH) and grant number N00014-09-1-0250 awarded by the Office of Naval Research (NAVY/ONR). The government has certain rights in the invention.

Signed and Sealed this
Seventh Day of August, 2018

Andrei Iancu
*Director of the United States Patent and Trademark Office*